Figure 1:
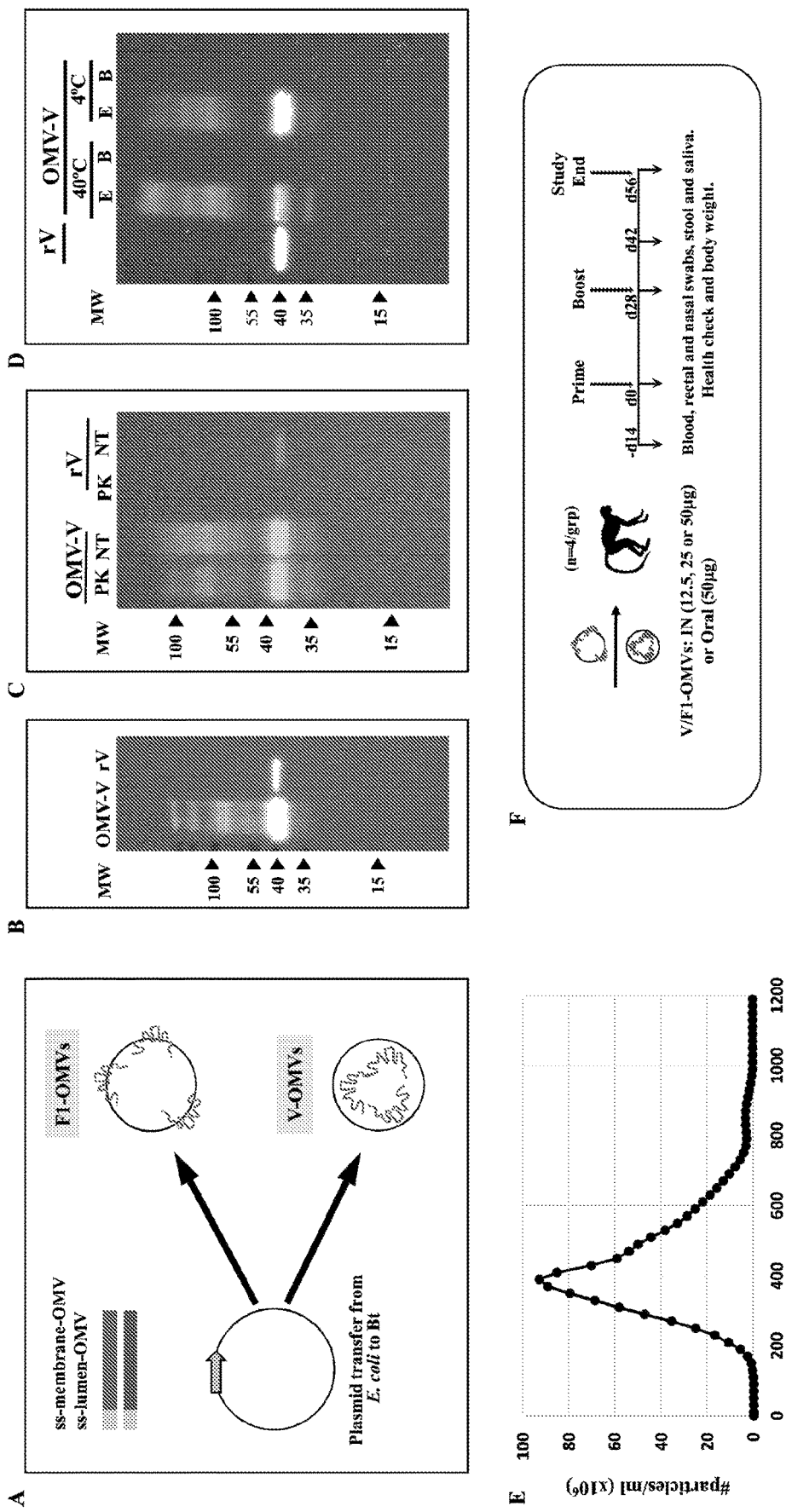

US012005106B2

(12) United States Patent
Stentz et al.

(10) Patent No.: US 12,005,106 B2
(45) Date of Patent: Jun. 11, 2024

(54) GUT BACTERIA DERIVED MICROVESICLES FOR VACCINE DELIVERY

(71) Applicant: Quadram Institute Bioscience, Norwich (GB)

(72) Inventors: Regis Stentz, Norwich (GB); Simon Carding, Norwich (GB)

(73) Assignee: Quadram Institute Bioscience, Norwich (GB)

( * ) Notice: Subject to any disclaimer, the term of this patent is extended or adjusted under 35 U.S.C. 154(b) by 0 days.

(21) Appl. No.: 17/309,067

(22) PCT Filed: Oct. 22, 2019

(86) PCT No.: PCT/GB2019/053007
§ 371 (c)(1),
(2) Date: Apr. 20, 2021

(87) PCT Pub. No.: WO2020/084295
PCT Pub. Date: Apr. 30, 2020

(65) Prior Publication Data

US 2022/0105168 A1 Apr. 7, 2022

(30) Foreign Application Priority Data

Oct. 22, 2018 (GB) ..................................... 1817194

(51) Int. Cl.

| | |
|---|---|
| *A61K 39/02* | (2006.01) |
| *A61K 39/112* | (2006.01) |
| *A61P 37/04* | (2006.01) |
| *C12N 15/74* | (2006.01) |
| *A61K 39/00* | (2006.01) |

(52) U.S. Cl.
CPC ...... *A61K 39/0275* (2013.01); *A61K 39/0291* (2013.01); *A61P 37/04* (2018.01); *C12N 15/74* (2013.01); *A61K 2039/523* (2013.01); *A61K 2039/542* (2013.01); *A61K 2039/543* (2013.01); *A61K 2039/55594* (2013.01); *A61K 2039/575* (2013.01)

(58) Field of Classification Search
None
See application file for complete search history.

(56) References Cited

FOREIGN PATENT DOCUMENTS

| | | | |
|---|---|---|---|
| WO | 2017087811 | A1 | 5/2017 |
| WO | 2017187190 | A1 | 11/2017 |

OTHER PUBLICATIONS

Carvalho et al (Clin. Experimental Immunology. 2019. 196: 287-304).*
"Efficacy Trials of Plague Vaccines: Endpoints, Trial Design, Site Selection", WHO Workshop, INSERM, Paris, France, 13 pages, Apr. 23, 2018.
International Bureau in connection with PCT/GB2019/053007 filed Oct. 22, 2019, "International Preliminary Report on Patentability", 11 pages, dated May 6, 2021.
Carvalho et al., "Use of Bioengineered human commensal gut bacteria-derived microvesicles for mucosal plague vaccine delivery and immunization", Clinical and Experimental Immunology, doi:10.1111/cei.13301, 18 pages, 2019.

* cited by examiner

*Primary Examiner* — Jennifer E Graser
(74) *Attorney, Agent, or Firm* — McKee, Voorhees & Sease, PLC

(57) ABSTRACT

The present invention relates to a vaccine suitable for immunisation against influenza, plague or *Y. pestis* infection said vaccine comprising outer membrane vesicles (OMVs) and the plague vaccine including the V and/or F1 antigens of *Y. pestis*.

6 Claims, 18 Drawing Sheets

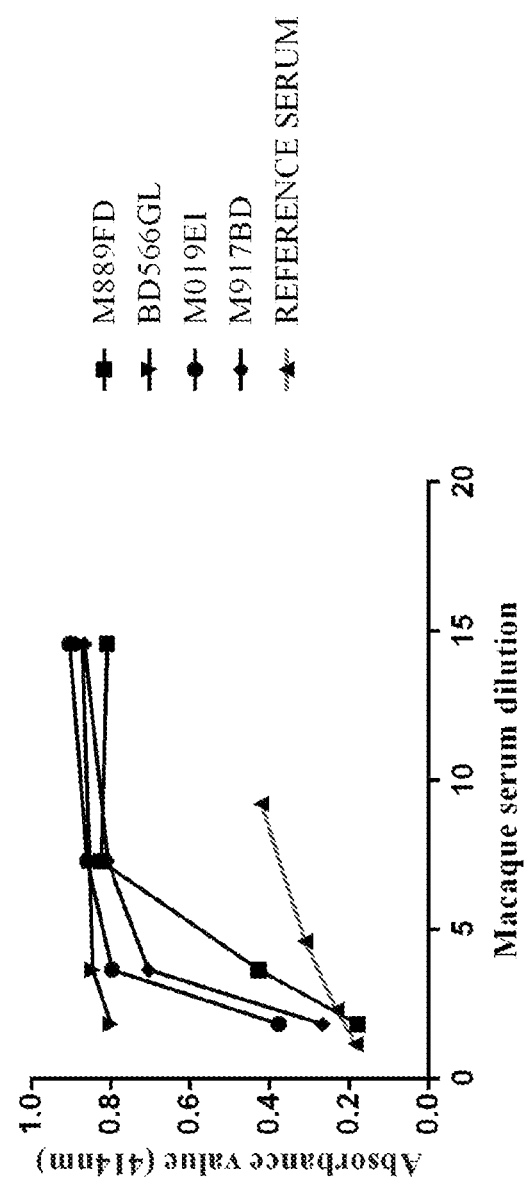

A.

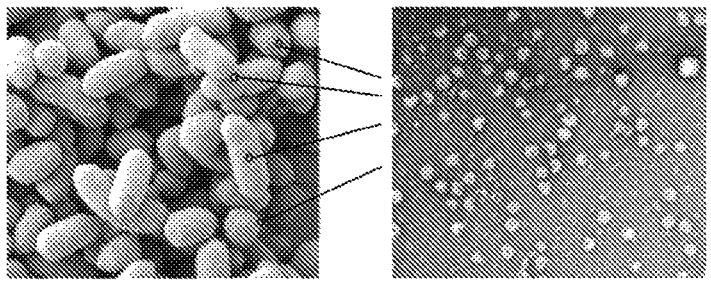

B.

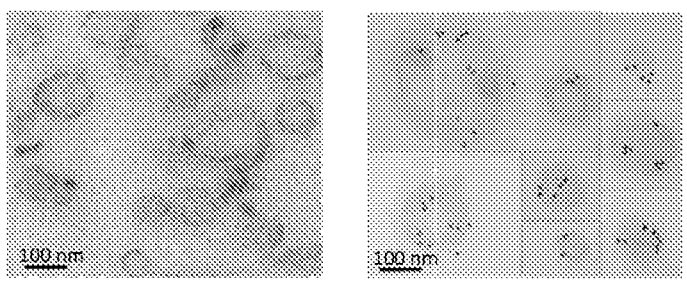

C.

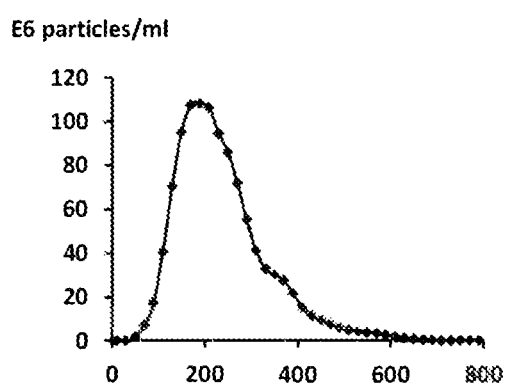

D.

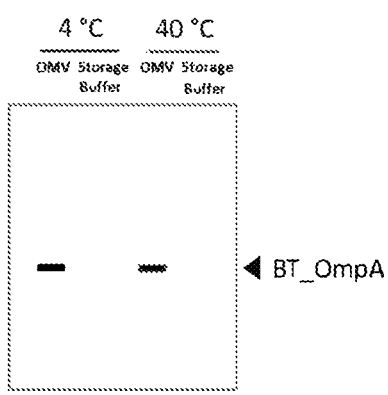

Fig. 8  Size, structure and stability of Bt OMVs. (a) Electron microscopy (EM) of Bt cells showing vesicles budding from their surface before release into the milieu (lines in left panel), and EM image of OMVs extracted from cell culture supernatant (right panel). (b) Immunodetection of native Bt OMVs using colloidal gold anti-rabbit Ig to detect binding of rabbit anti-Bt OmpA antisera (right panel). Left panel shows absence of staining of OMVs produced by an OmpA deletion mutant of Bt. (c) Size distribution of OMVs produced by *Bt* determined by nanoparticle tracking analysis. (d) The thermostability of OMVs was assessed after storage of OMV suspensions at 4°C or 40°C for 30 days. Immunoblotting for the detection of OmpA was performed on OMV extracts and storage buffer (SB).

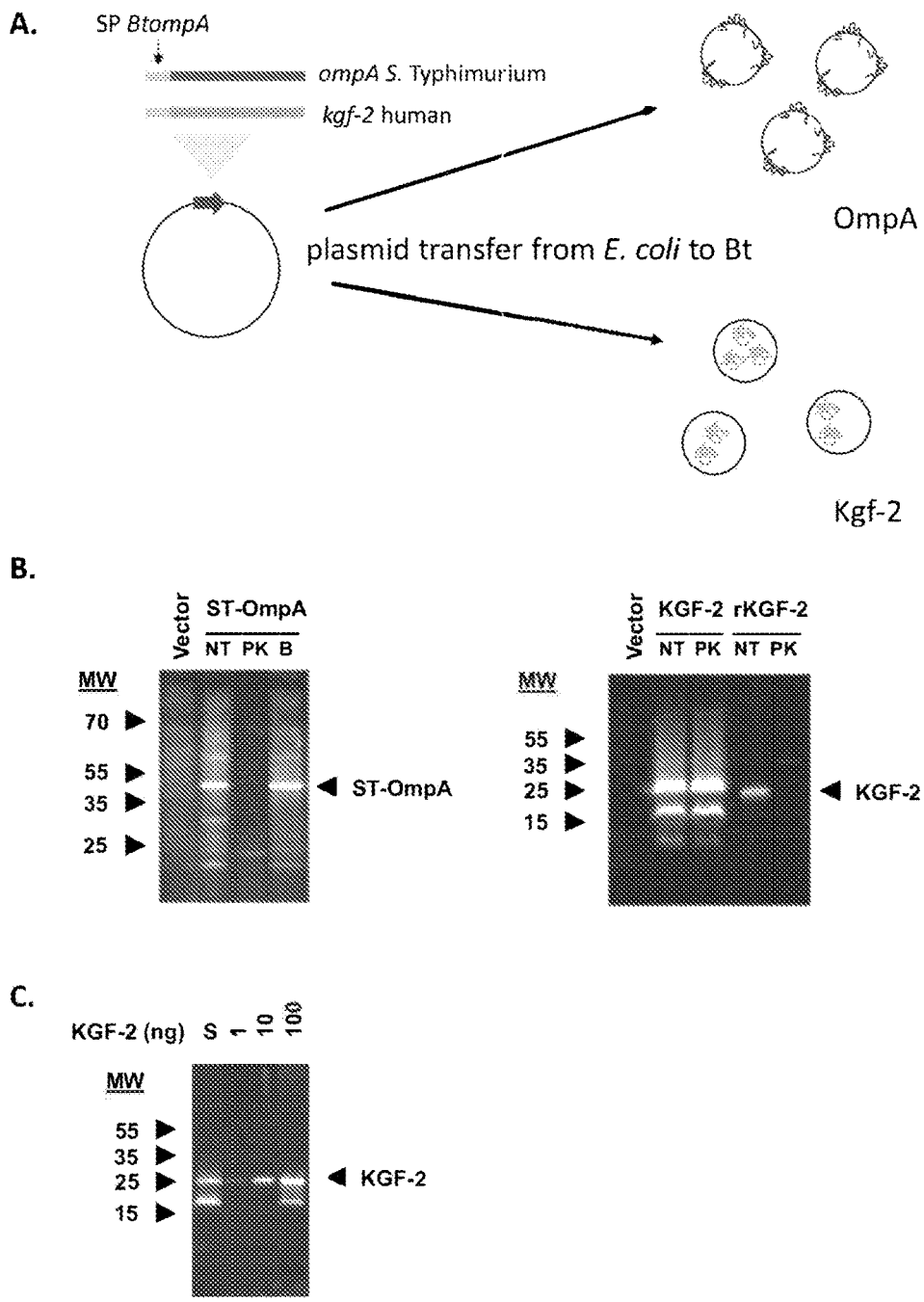

Fig. 9 Expression of heterologous proteins in Bt OMVs. (a) Schematic of cloning procedure for the secretion of proteins of interest in the lumen or at the surface membrane of OMVs. The secretion peptide of Bt OmpA (SP BtompA) is indicated in yellow and fused at the N-terminus of the gene of interest. (b) Determination of protein location after treatment with proteinase K (PK). Immunoblotting of STOmpA and KGF-2 with and without pre-treatment of OMV suspensions with proteinase K. NT: not treated; PK: + Proteinase K; B: PK buffer alone. (c) KGF-2 quantification within OMVs. Comparison of KGF-2 pure protein (1-100 ng) with 10 μl of 1 ml OMV suspension (S).

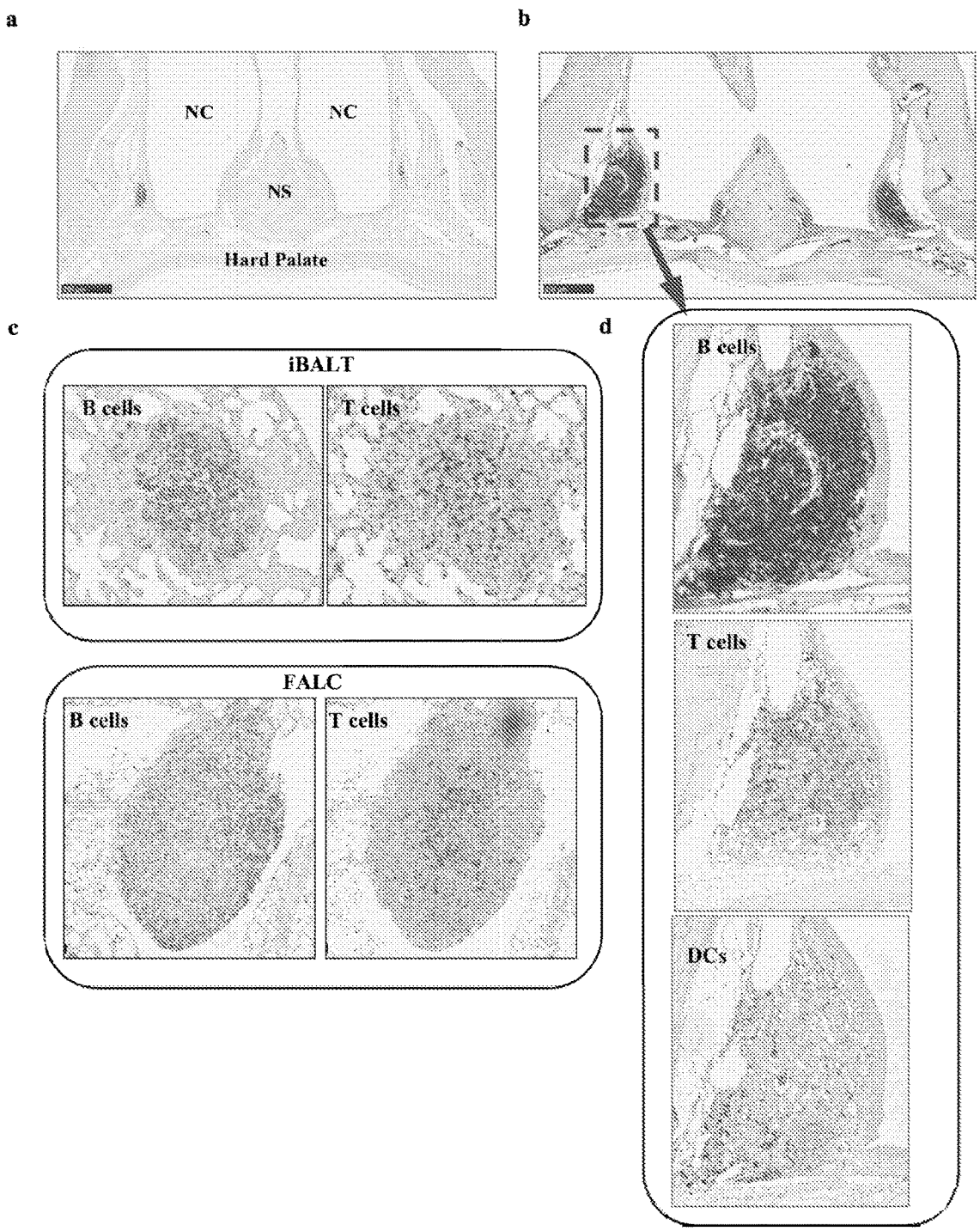

Fig. 10  Intrinsic adjuvanticity of Bt OMVs. Mice (n=5) were intranasally adminstered native PBS alone (a) or Bt OMVs in PBS (b) and 5 days later upper and lower respiratory tract tissue was processed for immuohistology to visualise immune cell activation and formation of organised lymphoid tissue containing $CD45R^+$ B cells, $CD3^+$ T cells and $Iba-1^+$ dendritic cells (DC) in the nasal associated lymphoid tissue (a, b and d), the inducible bronchus-associated lymphoid tissue (iBALT) (c), and fat associated lymphoid clusters (FALC) within the lung (d).

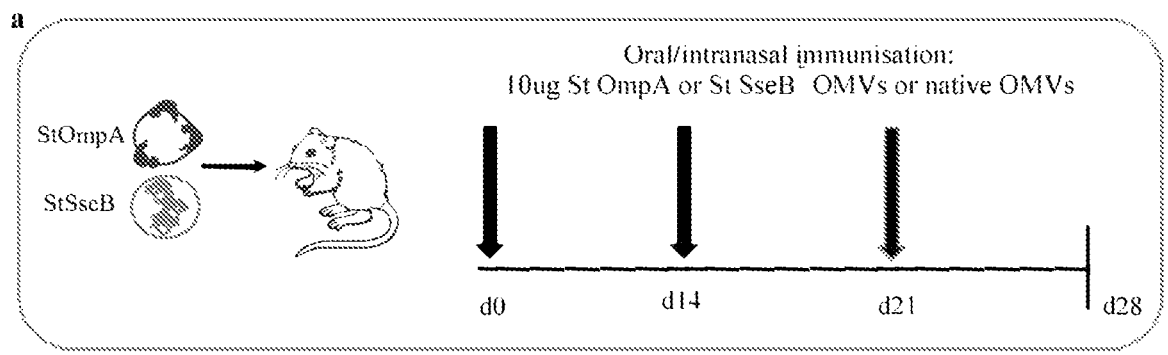
Fig. 11 Bt OMV-elicitied systemic and mucosal antibody responses. (a) Mice (n = 5-6/grp) were administered Bt OMVs expressing the *Salmonella* OmpA or SseB proteins via the oral (OG), intranasal (IN) or intraperitoneal (IP) routes according to the dosing reg Fig. 12 Bt OMVs expressing IAV H5F protein confer a level of protection to virus infection. Mice were immunised intranasally with H5F-OMVs in PBS, or as controls wild type OMVs or PBS alone and 28 days challenged intranasally with a lethal dose of PR8 virus. The weight of individual animals was assessed daily and at necropsy serum and brochoalveolar fluid (BAL) were analysed for IAV or H5 specific antibodies by ELISA. Lung homogenates were assessed for viral load (PFU). NS, no significant; *P<0.05; P<0.01; *P<0.001.

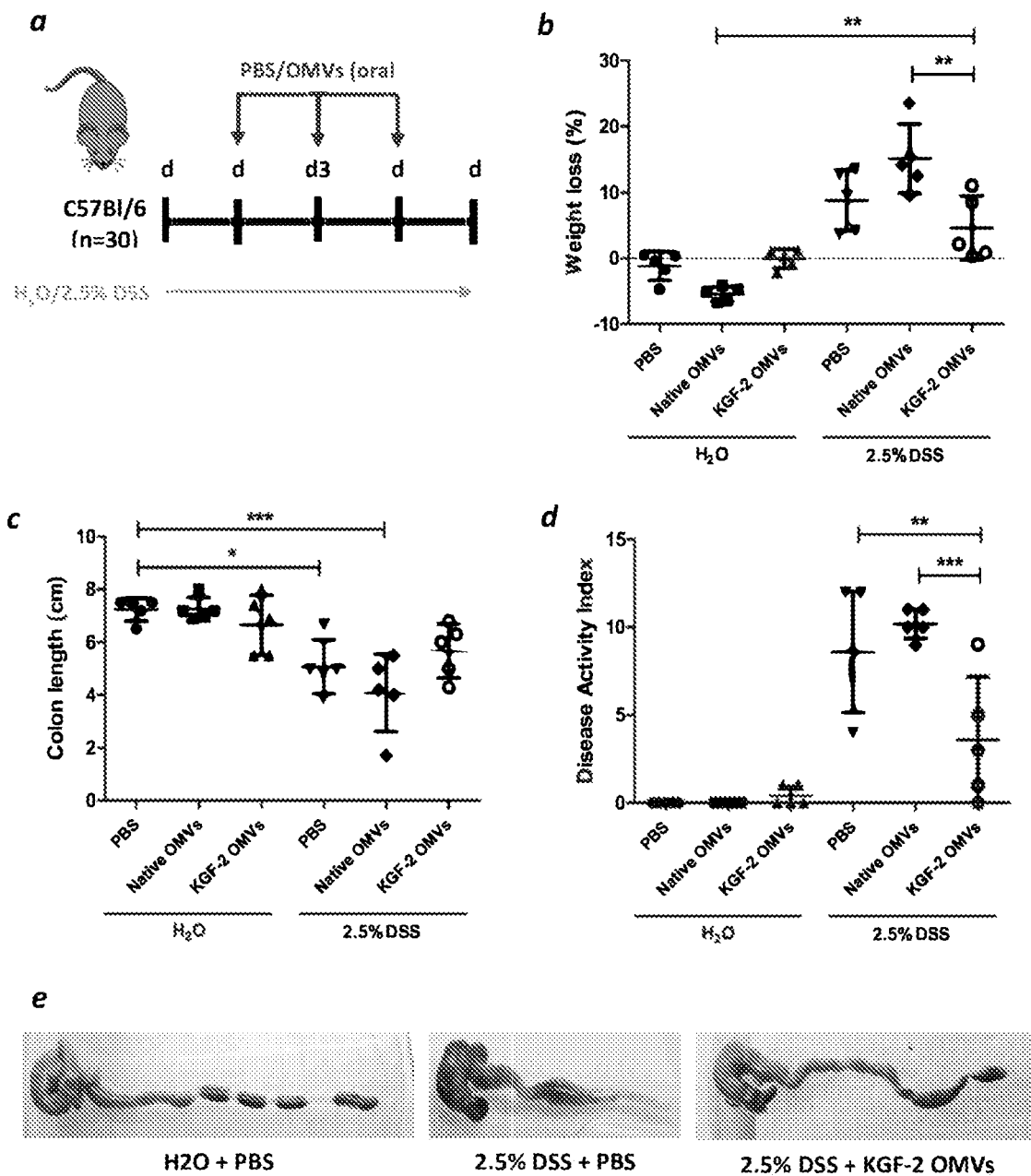

Fig. 13 OMVs containing KGF-2 ameleroate DSS-induced colitis. (a) Groups of mic were provided drinking water with or without 2.5% (w/v) DSS for 7 days. On days 1, 3 and 5 mice were orally gavaged with either PBS alone, native OMVs or OMVs containing KGF-2. (b) Percent weight loss at day 7. (c) Colon length at day 7. (d) Disease Activity Index (DAI) at day 7. (e) Representative images of colons. Data expressed as mean ± SD (n=5). Mice gavaged with PBS receiving regular drinking water were considered as the reference group for statistical analysis. NS, no significant; *$P<0.05$; $P<0.01$; *$P<0.001$.

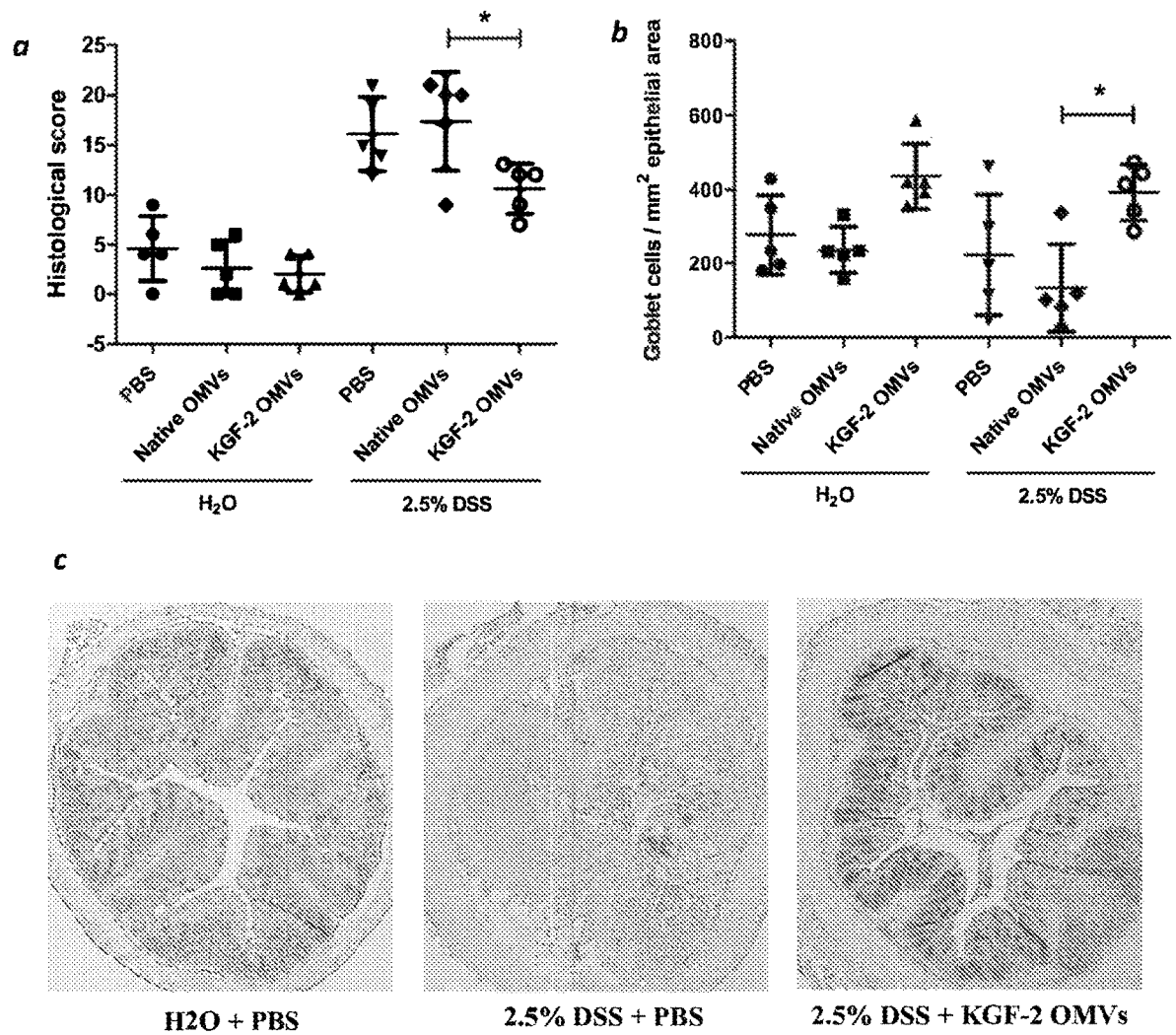

Fig. 14 OMVs containing KGF-2 protect and restore goble cells in DSS-induced colitis. (a) Histological score of colon tissue as determined by microscopy of H&E stained sections. (b) Number of Alcian Blue stained goblet cells per $mm^2$ of epithelial area. (c) Microscope images of goblet cell distribution in representative colon sections stained with Alcian Blue. Data expressed as mean ± SD (n=5). *P<0.05.

Supplementary Data

| Weight loss | Stool consistency | Bleeding | Caecum & colon appearance | Caecum & colon contents appearance | Score |
|---|---|---|---|---|---|
| <1% | Well-formed pellets | None | Normal | Regular shape | 0 |
| 1-5% | | | White, abnormal size, strictures | Irregular but formed | 1 |
| 5-10% | Loose | Slight | | Random shape | 2 |
| 10-15% | | | | Blood in colon | 3 |
| >15% | Diarrhoea | Gross | | Blood in caecum | 4 |

Fig. 15  Acquistion of fluorescent labelled Bt OMVs by lung macrophages and their subsequent trafficking to cervical and mediastinal lymph nodes after intranasal adminstration.

Disease Activity Index (DAI) criteria and scoring

| Category | | Criteria | Score |
|---|---|---|---|
| Inflammatory cell infiltrate | Severity | No infiltration | 0 |
| | | Minimal 0-10 % | 1 |
| | | Mild 10-25 % | 2 |
| | | Moderate 26-50 % | 3 |
| | | Marked > 51 % | 4 |
| | Extent | No infiltration | 0 |
| | | Mucosal | 1 |
| | | Mucosal and submucosal | 2 |
| | | Mucosal, submucosal and transmural | 3 |
| Presence of oedema | Extent | No oedema | 0 |
| | | in 0 to 25 % of the section | 1 |
| | | in 26 to 50 % of the section | 2 |
| | | in more than 51 % of the section | 3 |
| Epithelial changes | Goblet cell loss | None or increase | 0 |
| | | Minimal: 0-20 % | 2 |
| | | Mild: 21-35 % | 3 |
| | | Moderate: 36-50 % | 4 |
| | | Marked: > 50 % | 5 |
| | Erosion | Absence | 0 |
| | | Presence | 1 |
| Mucosal architecture | Extent | Irregular crypts | 4 |
| | | Crypt loss | 5 |

Fig. 16  Colon histology scoring

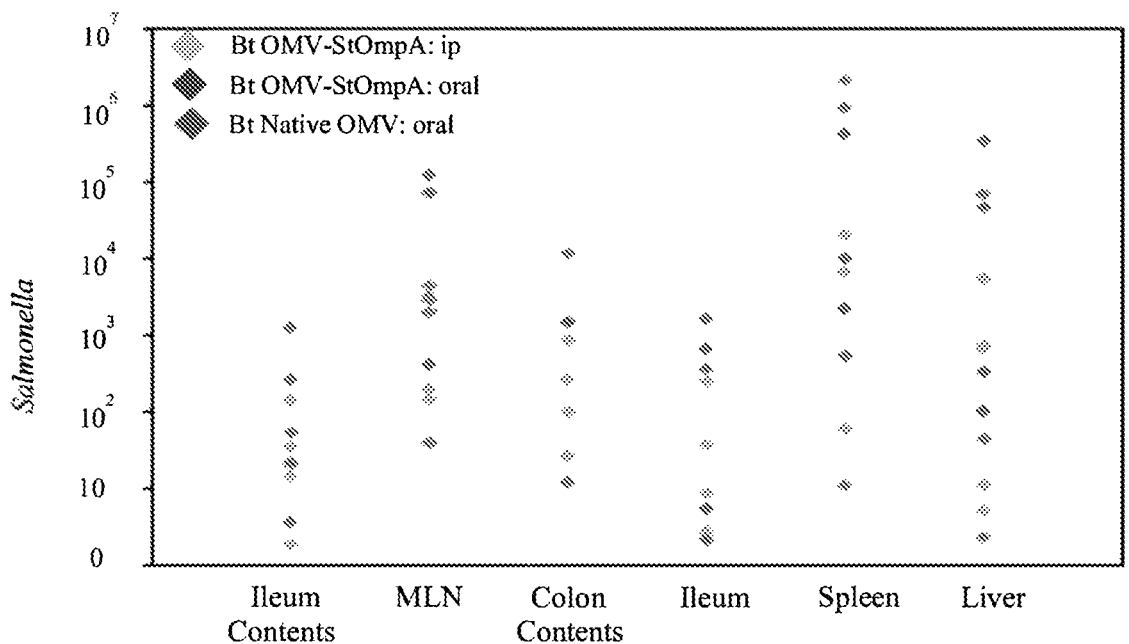

Fig. 17 Colonization of OMV-StOmpA immunised mice after *Salmonella* challenge. Mice immunised with Bt StOmpA-OMVs via the oral or parental (intraperitoneal; ip) route or that were orally administered native OMVs (see Materials and Methods for immunisation protocol) were challenged with an oral dose of $10^8$ CFU *Salmonella* typhimurium SL1344 and 5 days later the animals were euthanised and the bacterial load in the ileum and colonic contents, and homogenates of mesenteric lymph nodes (MLN), ileum tissue, spleen and liver were determined by plating serial dilutions on xylose lysine deoxycholate agar plates supplemented with 50 µg/ml streptomycin. The data shown represents sample CFU values for individual animals.

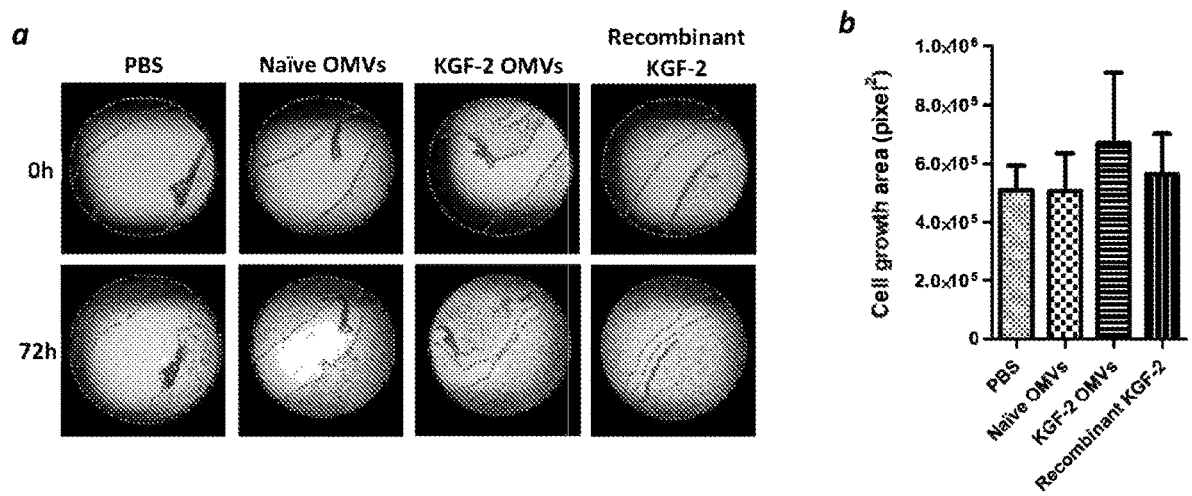

Fig. 18 Evaulating the biological activity of KGF-2 contained in Bt OMVs using an epithelial wound-healing assay. (a) Representative micrographs of healing of a scratch wound in a confluent monolayer of Caco2 cells after exposure to PBS, naïve OMVs, KGF-2 OMVs or recombinant KGF-2 for 72h. Red dotted lines demarcate the wound margin. (b) Graphical respresentation of cell growth across the wound area after 72h as determined by pixel$^2$.

GUT BACTERIA DERIVED MICROVESICLES FOR VACCINE DELIVERY

CROSS REFERENCE TO RELATED APPLICATIONS

This is a U.S. national phase application claiming priority to PCT/GB2019/053007, filed Oct. 22, 2019, which claims priority to British application 1817194.2, filed Oct. 22, 2018.

The invention to which this application relates is to the delivery of biologically active vaccine antigens directly to mucosal sites to inoculate against plague infection and/or influenza using stable microvesicles or outer membrane vesicles (OMVs) produced by the human commensal gut bacterium *Bacteroides thetaiotaomicron* (Bt).

The production of vesicles derived from the outer membrane of commensal bacteria using recombinant bacteria is disclosed in the applicant's co-pending application PCT/GB2017/051199 herein incorporated by reference.

Outer membrane vesicles (OMVs) are now known to be naturally produced and secreted by most Gram negative bacteria. Analyses of these 20-400 nm bilayered lipid membrane spherical structures have shown that they contain major components of the outer membrane such as lipopolysaccharide (LPS) and periplasmic contents of its' 'parent' bacteria.

Historically, OMVs have been associated with pathogenesis and the storing and transporting of virulence factors produced by major enteric Gram negative pathogens including *Helicobacter pylori* (VacA), *Shigella dysenteriae* (Shiga toxin) and enterohemorrhagic *E. coli* (ClyA).

Recently, this paradigm of OMV function has been questioned by evidence of a non-pathogenic, mutualistic role for OMVs produced by commensal gut bacteria. Members of the genus *Bacteroides* exclusively package carbohydrate and protein hydrolases in OMVs that appear to perform a "social function" in providing substrates for utilization by other bacteria and contributing to microbiota homeostasis. We have extended these observations providing evidence of a broader role of OMVs in gastrointestinal (GI)-tract homeostasis, and the ability of *Bacteroides*-derived OMVs to influence host immune and epithelial cell responses.

OMVs contain components that promote their interaction with host epithelial cells through numerous routes, including micropinocytosis, lipid raft- and clathrin-dependent endocytosis. OMVs produced by *B. fragilis* contain polysaccharide A that are sensed by dendritic cells via Toll Like Receptor (TLR) 2 leading to enhanced T regulatory cell activity and production of anti-inflammatory cytokines (IL-10) that contributes to protecting the host from experimental colitis [10]. Our own studies have demonstrated that mammalian intestinal epithelial cell (IEC) intracellular $Ca^{2+}$ signalling is activated by OMVs produced from the human commensal bacterium, *B. thetaiotaomicron* (Bt). We further found that $Ca^{2+}$ signalling was dependent upon a novel constituent of the OMVs: BtMinpp, a homologue of a mammalian inositol phosphate polyphosphatase cell-signalling enzyme. Collectively, these findings demonstrating a non-pathogenic and beneficial role for OMVs produced by commensal *Bacteroides* species are consistent with the packaging of bioactive macromolecules in OMVs to enable members of the intestinal microbiota to influence host cell physiology and establish bacteria-host mutualism.

It is feasible therefore that this pathway of host-microbe interaction mediated by OMVs could be exploited and used as an effective means of delivering biologically active proteins to the body and in particular to mucosal sites such as the GI- and respiratory tracts that are vulnerable to injury and disease as a result of exposure to noxious environmental chemicals and pathogens.

We have undertaken a proof-of-principle study to determine the suitability of using OMVs produced by *Bacteroides thetaiotaomicron* (Bt), a prominent member of the intestinal microbiota of all animals, to deliver bacteria-, virus- and human-derived proteins to the respiratory and GI-tract to protect against infection and tissue inflammation and injury using mouse models of respiratory influenza infection and we further describe the development of a novel drug delivery technology based upon engineering Bt to express in their OMVs antigens of *Y. pestis* for targeted delivery to a non-human primate (NHP) host.

Plague caused by the Gram negative bacterium, *Yersinia pestis,* is an ancient disease, accounting for many deaths over hundreds of years and still exists in parts of the world today. To protect against infection vaccines need to be able to elicit both humoural immunity and neutralising antibodies and cell-mediated immunity that is effective at primary, mucosal, sites of infection [1, 2].

There is currently no licensed plague vaccine in the Western world. Previously available US Pharmacopeia killed whole cell vaccines provided protection against bubonic but not pneumonic plague but due to unacceptable reactogenicity were discontinued [3]. Live-attenuated vaccines have been used in countries of the former Soviet Union and China although due to unacceptable reactogenicity to the vaccine and risk of reversion to full virulence they have not been licensed for use elsewhere including the USA [4]. The Fraction 1 (F1) and LcrV (virulence; V) *Y. pestis* proteins encoded by the Fra/pMT1 and pYV plasmids respectively [5], have been identified as major protective antigens that are essential for preventing phagocytosis of the bacteria and regulating type three secretion, respectively [6]. The present emphasis on developing F1 and V based vaccines is on recombinant protein-based subunit vaccines (rF1V) that incorporate chemical adjuvants. These can provide good protection in pre-clinical animal models [7, 8] although the F1-V fusion vaccine does not protect against F1 strains with modifications to the type III secretion system, and the duration of protection against pneumonic infection is also uncertain [9]. Injections and the use of needles for delivering these and other current vaccines has the associated risks of contamination, lack of patient compliance and high cost of mass immunisation, and a requirement for cold chain delivery and storage. Importantly, injected vaccines may also provide partial or no protection at primary, mucosal, sites of plague infection [2, 10]. Collectively these issues constrain the use of existing plague vaccines particularly in resource-poor low income settings.

Another approach to developing more effective mucosal vaccines for pathogens such as plague is using nanoparticle-based platforms. These include virus like particles, immune stimulating complexes, polymeric nanoparticles, inorganic nanoparticles, liposomes, and emulsions that have the capability of overcoming the high production costs and safety concerns of live vaccines in addition to the often weak immunogenicity and adjuvanticity of subunit and recombinant protein based vaccines [10]. These nanoscale carrier technologies enable conformationally correct antigens to be incorporated into highly stable nanoparticles that can control the spatial and temporal presentation of antigens to the immune system leading to their targeted and sustained release. An overlooked component of platform nanoscale vaccines are bacterial microvesicles and in particular, outer membrane vesicles (OMVs) of Gram-negative bacteria [11]. While many synthetic nanoparticles are capable of transferring heterologous antigens to antigen presenting cells (APC), the ability to efficiently stimulate the immune system is often not inherent [12]. OMVs, however, can combine high stability with antigen presentation and native adjuvanticity, making them an attractive vaccine platform [13].

Vesiculation and outer membrane vesicle (OMV) production is a fundamental characteristic of Gram-negative bacteria unrelated to bacterial lysis or membrane instability that full fills key requirements of a prokaryotic secretion process [14]. Nanoscale OMV proteoliposomes containing immunogenic components derived from the bacterial outer membrane and periplasm target APC, including dendritic cells [15-17] leading to T cell and B cell immunity. Research with OMVs from pathogenic bacteria including *Neisseria meningitides* and *Vibrio cholera* supports the case of OMVs as vaccine candidates [18] with those derived from *N. meningitides* having proven safety and efficacy records in controlling serogroup B meningococcal (MenB) disease outbreaks [19, 20]. Thus, OMV based vaccines offer significant advantages over conventional vaccines; they are non-replicating, provide needle-free delivery, target mucosal sites, have an established safety record, can elicit innate and antigen-specific adaptive immune responses, and possess self-adjuvant properties (i.e. microbe associated molecular pattern molecules [MAMPs] such as lipopolysaccharide [LPS]). The limitations of current, pathogen-derived, OMV vaccines are the potential for unintended toxicity due to associated toxins, low expression levels of protective antigens, variable efficacy depending on source and formulation, the need for exogenous adjuvants, and providing only incomplete protection because of strain variation. These limitations could in principle be overcome through the use of non-pathogenic OMV-producing commensal bacteria, engineered to improve their vaccine application. The recent demonstration that OMVs produced by the prominent human commensal gut bacteria *Bacteroides thetaiotaomicron* (Bt) access and influence intestinal epithelial and immune cells [21, 22] supports this proposition and identifies a means by which commensal gut bacteria can influence host cell physiology.

It is therefore an aim of the present invention to provide a vaccine or inoculation effective against plague or *Y. pestis* infection which addresses the abovementioned problems.

It is a second aim of the present invention to provide a method of producing a vaccine or inoculation which addresses the abovementioned problems.

It is a third aim of the present invention to provide a method of vaccination or inoculation against plague or *Y. pestis* infection.

It is therefore a further aim of the present invention to provide a vaccine or inoculation effective against influenza infection.

It is a yet further aim of the present invention to provide a method of producing an influenza vaccine or inoculation which addresses the abovementioned problems.

It is a yet further aim of the present invention to provide a method of vaccination or inoculation against influenza infection.

In a first aspect of the invention there is provided a vaccine suitable for immunisation against plague or *Y. pestis* infection said vaccine comprising outer membrane vesicles (OMVs) including the V and/or F1 antigens of *Y. pestis*.

Typically the OMVs are produced by gram-negative bacteria. Further typically the gram-negative bacteria are human commensal gut bacteria.

Preferably the OMVs are produced by bacteria from the genus *Bacteroides*. Further preferably the OMVs are produced by *Bacteroides thetaiotaomicron* (Bt).

Typically genes or mini-genes encoding the V and/or F1 *Y. pestis* proteins were cloned downstream of sequences encoding the N-terminal signal peptides of the OMV protein OmpA (BT_3852). Further typically the protein products are contained within the lumen or outer membrane of OMVs.

Typically the gene constructs are generated in *E. coli* hosts and then introduced into Bt.

In one embodiment a synthetic gene construct of 1043 bp encoding the V antigen and/or a synthetic operon construct of 3826 bp encoding caf1M, caf1A and/or caf1 genes of the caf1 operon that generates the F1 protein were N-terminally fused to the OmpA signal peptide of Bt. Typically this creates a construct in silico with codon usage being optimised for expression in the same species.

In one embodiment signal peptide prediction is used.

In one embodiment the resulting gene cassettes were obtained through gene synthesis and subsequently cloned into the *E. coli* plasmid pEX-A2 and pEX-K4 respectively.

Typically the cassettes contain BspHI and/or EcoRI restriction sites at their 5' and 3' ends, respectively. Typically the genes encoding V1 and/or F1 were excised from the pEX derivatives using BspHI and/or EcoRI. Further typically the genes were ligated into the NcoI/EcoRI-restricted pGH090 expression vector, resulting in pGH179 and pGH180 respectively.

In one embodiment the V and/or F1 containing OMVs have an average size of substantially 400 nm.

Typically, the V and/or F1 containing OMVs exhibit thermostability. Further typically the OMVs exhibit minimal loss of vaccine antigen content after storage for 6 weeks at 4° C. or 40° C.

In one embodiment the vaccine is delivered to the gastrointestinal (GI) tract. In a preferred embodiment the vaccine is delivered to the respiratory tract.

In a second aspect of the invention there is provided a method of producing a vaccine or inoculation, said method including the step of introducing at least part of the gene sequence encoding V and/or F1 antigens of *Y. pestis* into a gene sequence for OMV production.

In a third aspect of the invention there is provided a method of vaccination or inoculation against plague or *Y. pestis* infection, said method including the steps of introducing an OMV including the V and/or F1 antigens of *Y. pestis* to the body.

Typically oral and/or nasal administration are the preferred routes of vaccination. Further typically this generates protective immunity at primary sites of plague infection.

In one embodiment for oral delivery a dose of 50 μg of V antigen was used. Preferably the dose was formulated in Bt OMVs.

In a further aspect of the invention there is provided a vaccine suitable for immunisation against influenza infection said vaccine comprising outer membrane vesicles (OMVs) characterised in that within and/or on the outer membrane of Bt OMVs both bacteria and/or virus derived vaccine antigens are delivered in a form capable of eliciting antigen specific immune and antibody responses in mucosal tissues and/or systemically.

In one embodiment BT OMV is produced using a synthetic gene construct. Typically the gene construct encodes a synthetic influenza strain. In one embodiment A 635 bp synthetic gene construct encoding a synthetic influenza (H5F; from IAV strain H5N1 (VN/04:A/VietNam/1203/04)) is used.

Typically, pre-fusion headless HA mini-stem N-terminal is fused to the OmpA signal peptide of Bt is created in silico.

Typically the resulting gene cassette is obtained through gene synthesis and subsequently cloned into *E. coli*. Further typically the *E. coli* plasmid pEX-K168 (Eurofins, Germany) is used.

In one embodiment the cassette contains BspHI and EcoRI restriction sites at its 5' and 3' ends, respectively. This allows allowing for the translational fusion of the gene to the start codon in the *Bacteroides* expression vector pGH090. Typically the gene is excised from pEX-K168 using BspHI and EcoRI and ligated into the NcoI/EcoRI-restricted pGH090 expression vector, resulting in pGH184.

Specific embodiments of the invention are now described with reference to the following figures:

FIG. 1. Bt OMV plague vaccines. A. Schematic of cloning procedure for the expression of *Yersinia* virulence proteins F1 and V at the surface or in the lumen, respectively, of Bt OMVs. The Bt secretion signal sequence is indicated in yellow and is fused at the N-terminus of the F1 and V genes. B. Expression of V antigen in OMV lysates determined by immunoblotting (IB). C. Determination of protein location after treatment with proteinase K (PK). IB of V antigen with and without pre-treatment of V-OMVs or recombinant V (rV) with proteinase K. NT: not treated. D. Thermostability of V-OMVs assessed by storing preparations at different temperatures for 8 weeks prior to analysing OMV extracts (E) or storage buffer (B) for presence of V antigen by IB. Molecular weight (MW) is expressed in kDa. E. Size distribution of Bt V-OMVs by nanoparticle tracking analysis. The OMV suspension was diluted 100 times. F. Schematic of OMV-plague vaccine NHP immunisations via the intranasal (IN) or oral route and analyses.

FIG. 2. Systemic and humoral response to F1-OMV vaccines. Serum (A) and saliva (B) from animals prior to (pre) and 56 days post immunization with F1-OMVs were analysed for F1-specific IgG and IgA antibodies, respectively by ELISA. Bronchoalveolar lavage fluid (BAL) (C) and salivary gland homogenates (D) were analysed for antigen-specific IgA at the study end point. The data shown represents mean±SEM values.

FIG. 3. Humoral systemic immune response to V-OMV vaccines. The amounts and titre of V-antigen specific IgG in the sera of animals immunised with V-OMVs via the intranasal or oral route was determined prior to immunisation (day −14 and day 0) and at three different timepoints post immunisation (days, 28, 42 and 56) by ELISA using an initial serum dilution of 1:10 prior to serial 1 in 4 dilutions. Each line graph represents the mean value for each group (n=4). The levels of V-specific IgG in individual animals immunised with 25 mg of V-OMVs via the intranasal route is shown in the bottom right graph with the horizontal lines in each category representing the mean±SEM.

FIG. 4. Mucosal humoral immune response to V-OMV vaccine. A. The amounts and titre of V-antigen specific IgA in the saliva of animals immunised with V-OMVs via the intranasal or oral route was determined prior to immunisation (day 0) and at three different timepoints post immunisation (days, 28, 42 and 56) by ELISA using serial 1 in 2 dilutions. Each line graph represents the mean value for each group (n=4). B. Levels of V-specific IgA in saliva samples of individual animals immunised with 25 μg of V-OMVs via the intranasal route. The horizontal lines in each category representing the mean±SEM. C. Levels of V-specific IgA in salivary glands and bronchoalveolar lavage (BAL) samples for animals immunised intranasally or orally with V-OMVs analysed at day 56 post immunisation.

FIG. 5. Cytokine production by PBMCs from V-OMV immunized animals. PBMCs obtained from animals previously immunised with V-OMVs via the intranasal (IN) or oral at day 56 post immunisation were cultured in the presence or absence (PBS) of recombinant V protein (rV) for 72 hours after which supernatants were analysed for cytokine content using a multiplex bead assay and flow cytometry. Limit of detection for given values was IL-1β <1.11 pg/mL, MCP-1 <1.61 pg/mL, IL-6 <1.45 pg/mL, IL-8 <1.02 pg/mL, IL-23 <1.44 pg/ml. Given values represent the group means±SEM of duplicate samples, n=4 per group. *$p \leq 0.05$, *$p \leq 0.001$, **$p \leq 0.0001$.

FIG. 6. Principal coordinates analysis for weighted UniFrac distance metrics for 16S rRNA sequences obtained from animals immunised with V-OMVs to visualise the degree of relatedness between samples. A. The blue symbols represent the faecal microbiotas (blue) of individual animals immunised with V-OMVs via the oral route and the red symbols representing the nasal microbiota of animals immunised with V-OMVs via the intranasal route. B. The nasal microbiotas of animals pre-(circles) and post (squares) V-OMV intranasal immunisation. The colours indicate different doses of V-OMVs.

FIG. 7. A competitive ELISA assay to assess the functionality of immune sera from V-OMV immunised animals. Serial dilutions of sera from animals immunised with V-OMVs identified by individual code numbers shown in the key were tested for their ability to displace a monoclonal V antibody from the surface of the V antigen immobilised in microtitre plate wells. Reference serum was from NHPs immunised intramuscularly with recombinant F1 and V plus adjuvant.

FIG. 8. Size, structure and stability of Bt OMVs. (a) Electron microscopy (EM) of Bt cells showing vesicles budding from their surface before release into the milieu (lines in left panel), and EM image of OMVs extracted from cell culture supernatant (right panel). (b) Immunodetection of native Bt OMVs using colloidal gold anti-rabbit Ig to detect binding of rabbit anti-Bt OmpA antisera (right panel). Left panel shows absence of staining of OMVs produced by an OmpA deletion mutant of Bt. (c) Size distribution of OMVs produced by Bt determined by nanoparticle tracking analysis. (d) The thermostability of OMVs was assessed after storage of OMV suspensions at 4° C. or 40° C. for 30 days. Immunoblotting for the detection of OmpA was performed on OMV extracts and storage buffer (SB).

FIG. 9. Expression of heterologous proteins in Bt OMVs. (a) Schematic of cloning procedure for the secretion of proteins of interest in the lumen or at the surface membrane of OMVs. The secretion peptide of Bt OmpA (SP BtompA) is indicated in yellow and fused at the N-terminus of the gene of interest. (b) Determination of protein location after treatment with proteinase K (PK). Immunoblotting of STOmpA and KGF-2 with and without pre-treatment of OMV suspensions with proteinase K. NT: not treated; PK: + Proteinase K; B: PK buffer alone. (c) KGF-2 quantification within OMVs. Comparison of KGF-2 pure protein (1-100 ng) with 10 μl of 1 ml OMV suspension (S).

FIG. 10. Intrinsic adjuvanticity of Bt OMVs. Mice (n=5) were intranasally administered native PBS alone (a) or Bt OMVs in PBS (b) and 5 days later upper and lower respiratory tract tissue was processed for immunohistology to visualise immune cell activation and formation of organised lymphoid tissue containing $CD45R^+$ B cells, $CD3^+$ T cells and Iba-$1^+$ dendritic cells (DC) in the nasal associated lymphoid tissue (a, b and d), the inducible bronchus-associated lymphoid tissue (iBALT) (c), and fat associated lymphoid clusters (FALC) within the lung (d).

FIG. 11. Bt OMV-elicited systemic and mucosal antibody responses. (a) Mice (n=5-6/grp) were administered Bt OMVs expressing the *Salmonella* OmpA or SseB proteins via the oral (OG), intranasal (IN) or intraperitoneal (IP) routes according to the dosing regimen described in the Material and Methods section. At autopsy, serum (b) and bronchoalveolar lavage fluid (BAL) (c) were analysed for anti-OmpA and anti-SseB IgG and IgA antibody titres, respectively, by ELISA. The boxplots identify the mean and upper and lower quartile values for data sets obtained from animals within each treatment group. Analysis of variance for multiple comparisons of means between independent samples (ANOVA) was followed by a Tukey's test. ***$P<0.001$; ns=non-significant differences. Total IgA levels in BAL (d) and salivary gland (e) samples from animals treated with StOmpA OMVs or PBS (control) were determined by ELISA using IgA standards as described in the Materials and Methods section.

FIG. 12. Bt OMVs expressing IAV H5F protein confer a level of protection to virus infection. Mice were immunised intranasally with H5F-OMVs in PBS, or as controls wild type OMVs or PBS alone and 28 days challenged intranasally with a lethal dose of PR8 virus. The weight of individual animals was assessed daily and at necropsy serum and bronchoalveolar fluid (BAL) were analysed for IAV or H5 specific antibodies by ELISA. Lung homogenates were assessed for viral load (PFU). NS, no significant; *$P<0.05$; $P<0.01$; *$P<0.001$.

FIG. 13. OMVs containing KGF-2 ameliorate DSS-induced colitis. (a) Groups of mic were provided drinking water with or without 2.5% (w/v) DSS for 7 days. On days 1, 3 and 5 mice were orally gavaged with either PBS alone, native OMVs or OMVs containing KGF-2. (b) Percent weight loss at day 7. (c) Colon length at day 7. (d) Disease Activity Index (DAI) at day 7. (e) Representative images of colons. Data expressed as mean±SD (n=5). Mice gavaged with PBS receiving regular drinking water were considered as the reference group for statistical analysis. NS, no significant; *$P<0.05$; $P<0.01$; *$P<0.001$.

FIG. 14. OMVs containing KGF-2 protect and restore goblet cells in DSS-induced colitis. (a) Histological score of colon tissue as determined by microscopy of H&E stained sections. (b) Number of Alcian Blue stained goblet cells per mm$^2$ of epithelial area. (c) Microscope images of goblet cell distribution in representative colon sections stained with Alcian Blue. Data expressed as mean±SD (n=5). *$P<0.05$.

FIG. 15. Acquisition of fluorescent labelled Bt OMVs by lung macrophages and their subsequent trafficking to cervical and mediastinal lymph nodes after intranasal administration.

FIG. 16. The impact of orally administered Bt OMVs on the recipients intestinal microbiota. Mice (n=5) were oral gavaged with native OMVs on day 3, 5 and 7, and faeces collected on day 0, 4, 7 and 8 to evaluate the impact of the OMVs on the host microbiota. Faeces were weighed, homogenized in PBS and serially diluted prior to plating on different agar media: Nutrient=total aerobes, Wilkinschalgren=total anaerobes, Brain Heart Infusion (BHI)=total anaerobes and BHI supplemented with gentamicin and amikacin=*Bacteroides*. The results are expressed as the logarithm of the CFU normalized to the weight of individual faecal samples for each day and growth medium. Data is expressed as mean±SD. Statistical significance differences were evaluated using Dunnett bilateral post-hoc to compare days after OMV administration vs. the control day 0. *$P<0.05$; **$P<0.01$.

FIG. 17. Colonization of OMV-StOmpA immunised mice after *Salmonella* challenge. Mice immunised with Bt StOmpA-OMVs via the oral or parental (intraperitoneal; ip) route or that were orally administered native OMVs (see Materials and Methods for immunisation protocol) were challenged with an oral dose of 10$^8$ CFU *Salmonella typhimurium* SL1344 and 5 days later the animals were euthanised and the bacterial load in the ileum and colonic contents, and homogenates of mesenteric lymph nodes (MLN), ileum tissue, spleen and liver were determined by plating serial dilutions on xylose lysine to deoxycholate agar plates supplemented with 50 μg/ml streptomycin. The data shown represents sample CFU values for individual animals.

FIG. 18. Evaluating the biological activity of KGF-2 contained in Bt OMVs using an epithelial wound-healing assay. (a) Representative micrographs of healing of a scratch wound in a confluent monolayer of Caco2 cells after exposure to PBS, naïve OMVs, KGF-2 OMVs or recombinant KGF-2 for 72 h. Red dotted lines demarcate the wound margin. (b) Graphical representation of cell growth across the wound area after 72 h as determined by pixel$^2$.

Referring firstly to the plague vaccine, plague caused by the Gram negative bacterium, *Yersinia pestis*, is still endemic in parts of the world today. Protection against pneumonic plague is the paramount requirement to prevent epidemic spread yet there is currently no licensed plague vaccine in the Western world. Here we describe the means of delivering biologically active plague vaccine antigens directly to mucosal sites of plague infection using highly stable microvesicles (outer membrane vesicles; OMVs) naturally produced by the prominent and harmless human commensal gut bacterium *Bacteroides thetaiotaomicron* (Bt). Bt was engineered to express in their OMVs the major plague protective antigens Fraction 1 (F1) in the outer membrane and LcrV (V) in the lumen for targeted delivery to the gastrointestinal (GI) and respiratory tracts in a non-human primate (NHP) host. The key findings of our study are that Bt OMVs stably expresses F1 and V plague antigens, and in particular the V antigen, in the correct, immunogenic form. V-OMVs delivered intranasally elicit substantive and specific immune and antibody responses both in the serum (IgG) and in the upper and lower respiratory tract (IgA), including the generation of serum antibodies able to kill plague bacteria. Our results also show that Bt OMV based vaccines posses many desirable characteristics of a plague vaccine including biosafety and absence of any adverse effects, pathology or gross alteration of resident microbial communities (microbiotas), high stability and thermo-tolerance, needle-free delivery, intrinsic adjuvanticity, the ability to stimulate both humoral and cell mediated immune responses, and targeting of primary sites of plague infection.

Nasal administration are the preferred routes of vaccination to generate protective immunity at primary sites of plague infection. To be effective, significant challenges including minimising loss of immunogenicity during transit and optimising dosing regimens and routes of delivery that safely generates protective antibodies must be met. To overcome these challenges we have developed a novel drug delivery technology platform that exploits the natural production of nanoscale microvesicles called outer membrane vesicles (OMVs) by the prominent human commensal gut bacterium *Bacteroides thetaiotaomicron* (Bt). Using a non-human primate model we have shown that Bt OMVs expressing the major plague protective antigens F1 and V when delivered nasally elicit abundant and specific antibodies in both the serum (IgG) and upper and lower respiratory tract (IgA) including antigen-specific IgG antibodies that were active in two independent surrogate assays of protection. Our results also highlight key advantages our Bt OMV vaccine technology offers over current plague vaccines in terms of technology and/or approach. These include their acellular non-infectious nature, needle free delivery, direct targeting of primary sites of mucosal plague infection, intrinsic adjuvanticity, activation of both the innate and adaptive arms of the immune system, and have no cold chain requirement.

Here we describe development of a novel drug delivery technology based upon engineering Bt to express in their OMVs the V and F1 antigens of *Y. pestis* for targeted delivery to the gastrointestinal (GI) and respiratory tracts in a non-human primate (NHP) host. Our findings demonstrate OMV-plague vaccines are an effective means of eliciting both mucosal and systemic antibody responses and systemic cell-mediated responses with delivery of OMV vaccines by the respiratory route being particularly effective at eliciting antigen-specific IgG antibodies that were active in two independent surrogate assays of protection.

Results

Study Design and Rationale

The aim of this feasibility study was to determine the suitability of OMVs produced by the human commensal gut bacteria, Bt, as a plague vaccine antigen delivery platform to activate mucosal and systemic immune responses in a non-human primate (NHP) host with the capability of protecting against plague infection. Although mice are a common experimental model system used in preclinical studies of human drugs and vaccines, the NHP is better suited to assess the particular questions concerning Bt OMV vaccine efficacy and safety as their respiratory and GI-tracts and natural diet (and hence microbiome) are far closer to that of humans. Their use therefore de-risks the development pathway for Bt-OMV vaccine by providing assurance that the NHP microbiome and histological integrity of the GI-tract and other associated tissues are not adversely affected after immunisation. In addition, the use of NHP antisera to demonstrate bactericidal activity would help pave the way for assessment of the protective effect of Bt OMV vaccination in humans as a surrogate for protection against infection.

Expression of *Y. pestis* Vaccine Antigens in Bt OMVs

Mini-genes encoding the V and F1 *Y. pestis* proteins were cloned downstream of sequences encoding the N-terminal signal peptides of the major OMV protein OmpA (BT_3852) whose products are contained within the lumen or outer membrane of OMVs (FIG. 1A). The constructs were generated in *E. coli* hosts and then mobilised into Bt via a triple filter mating protocol using a helper strain. Immunoblotting of whole cell and OMV lysates of recombinant Bt strains confirmed expression of the V antigen (FIG. 1B). Whilst it was not possible to detect the F1 protein by immunoblotting, we were able to confirm its expression by LC-MS proteomics of OMV lysates (data not shown). The luminal versus outer membrane distribution of the proteins in Bt OMVs was established using a protease protection assay which showed that V protein distribution was within the lumen of OMVs (FIG. 1C) whereas F1 expression was associated with the OMV outer membrane (data not shown). V and F1 containing OMVs had an average size of ~400 nm (FIG. 1E) and exhibited high thermostability with minimal loss of vaccine antigen content after storage for 6 weeks at 4° C. or 40° C. (FIG. 1D and data not shown).

OMV Immunisation Protocol

Oral and nasal administration are the preferred routes of vaccination to generate protective immunity at primary sites of plague infection [9]. We initially set out therefore to determine which of these routes was optimal for Bt OMV-plague vaccines as determined by measuring both local and systemic antigen-specific V and F1 IgA and IgG antibodies. For oral delivery we used a dose of 50 µg of V antigen formulated in Bt OMVs, which is mid-range of vaccine dose used previously in cynomolgus macaques [26] and is a human-equivalent dose and concentration [7]. In considering the potential risks of administering agents via the intranasal route and its accessibility to the systemic circulation and the brain, we used a range of OMV vaccines doses (12.5, 25 and 50 µg) to assess safety, tolerability and determine the lowest dose required to induce a strong immune response. OMV vaccination followed a prime and single boost dosing regimen as depicted in FIG. 1F.

Host Response to F1-OMV Plague Vaccines

Figure 2:
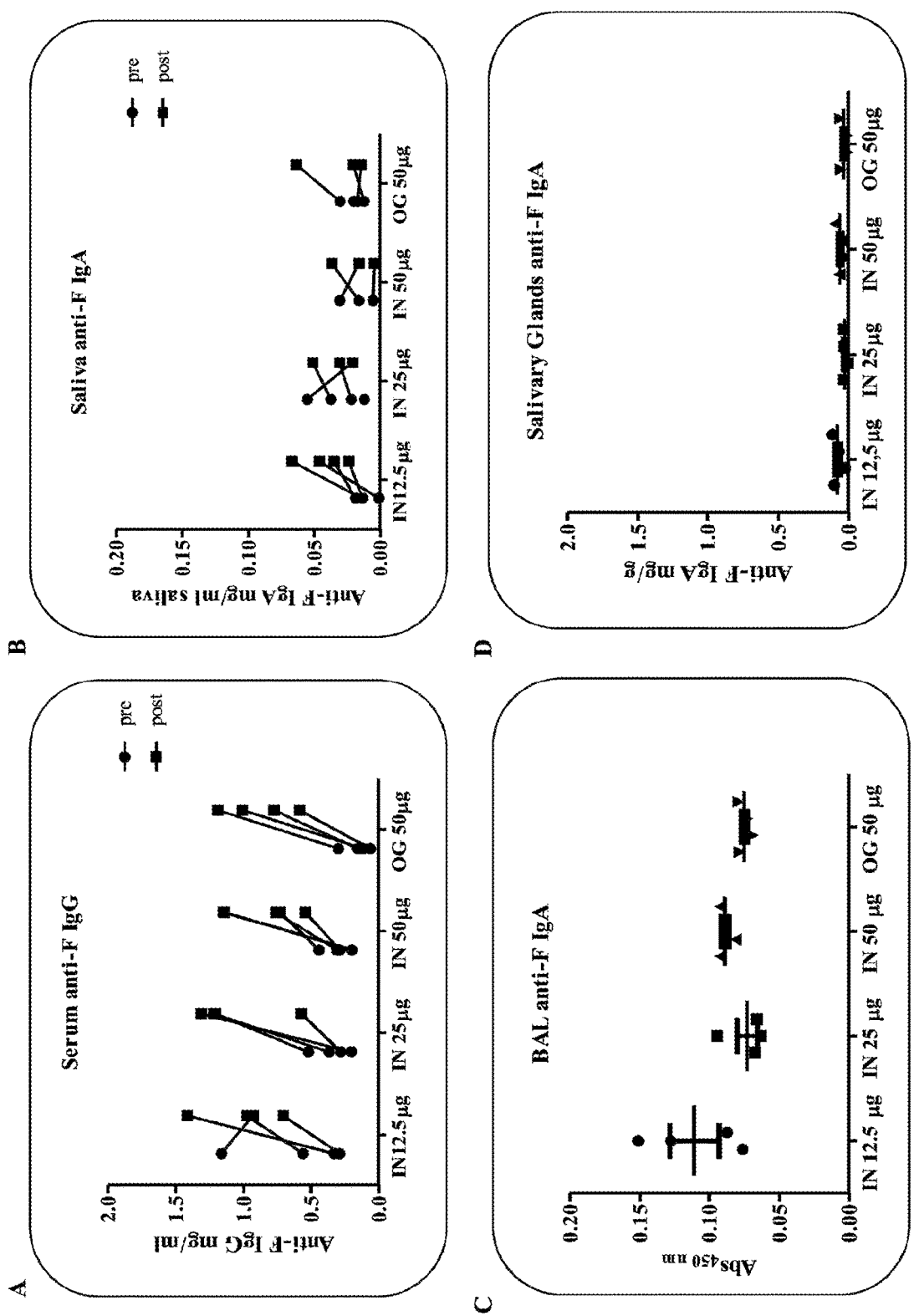

F1-OMV vaccine formulations were evaluated by measuring antigen-specific IgA and IgG levels in mucosal secretions and tissues and in the serum, respectively (FIG. 2). F1-OMVs generated antigen-specific IgG serum antibodies (~0.5-1.5 µg/ml) after both oral and intranasal immunisation with evidence of inter-individual variation in levels of F1 specific IgG in most experimental groups; whereas one animal administered 12.5 µg F1-OMVs intranasally failed to respond another had high levels of reactive antibodies prior to immunisation, at day –14, although this reactivity was no longer evident at day 0, returning to levels comparable with other animals. There was no evidence of an antigen dose or dependency in the levels of antibodies produced as similar levels of F1 specific IgG were seen in animals receiving 12.5, 25 or 50 µg of F1-OMVs (FIG. 2a). There was also no clear evidence for the superiority of oral versus nasal delivery of F1-OMVs in terms of levels of antigen specific IgG antibodies generated (FIG. 2A). F1-OMVs elicited weak mucosal immune responses with low levels of antigen specific IgA present in saliva (FIG. 2B) and BAL (FIG. 2C) samples irrespective of the route of administration. It was not possible to detect F1-specific IgA antibodies in the salivary glands of F1-OMV immunised animals (FIG. 2D).

Host Response to V-OMV Plague Vaccines

Figure 3:
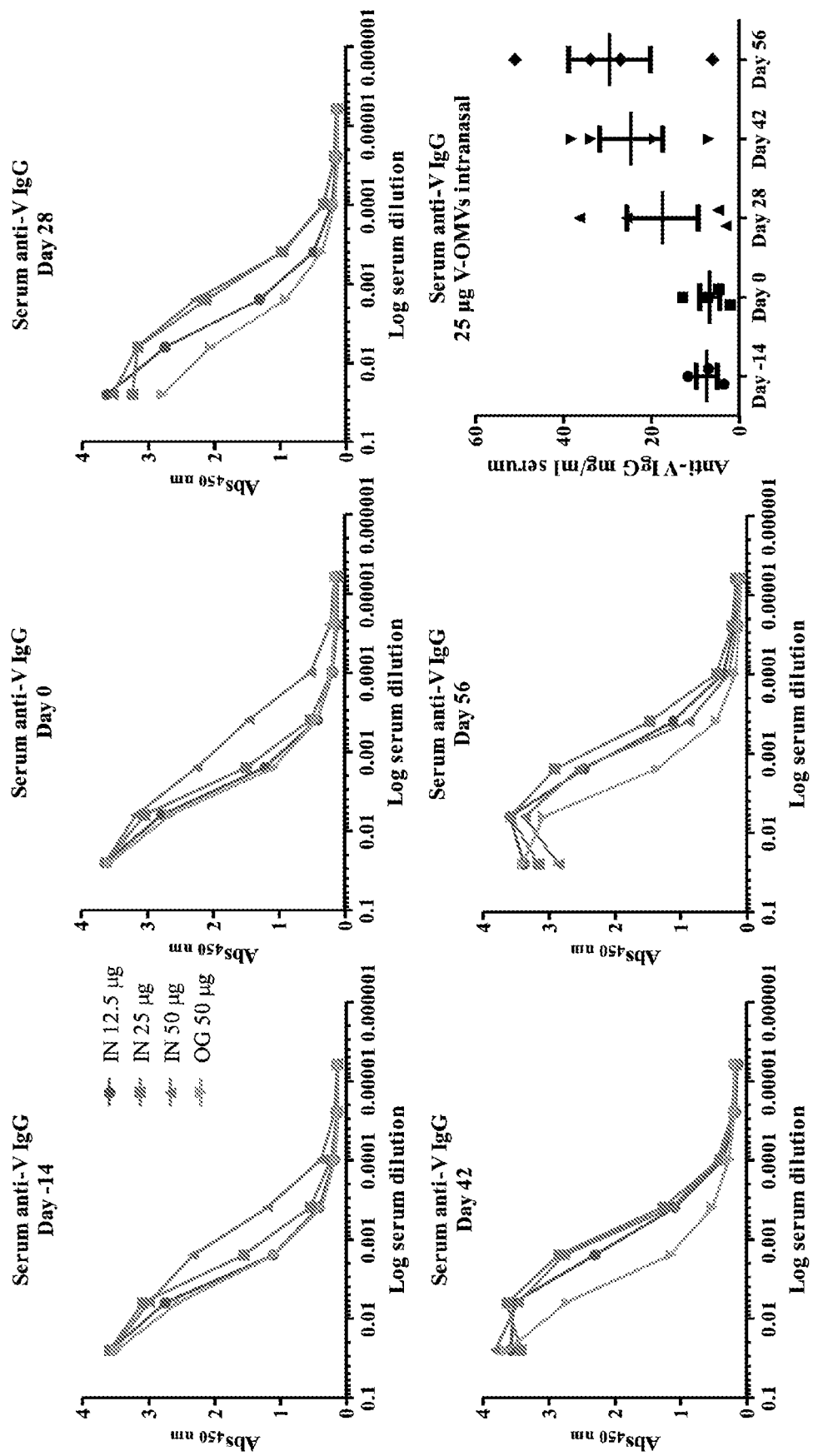

V-OMV vaccines generated strong antibody responses systemically and at mucosal sites (FIG. 3). Analysis of serum anti-V specific IgG antibodies showed that the intranasal route of V-OMV immunisation generated higher titres of antibodies compared to oral immunisation (FIG. 3); contrasting with the findings from F1-OMVs immunisations demonstrating no vaccine delivery route related differences in IgG responses (FIG. 2). The highest titres of V-specific IgG at the study end point were in animals intranasally vaccinated with 25 µg of V-OMV with antibody levels increasing over the study period (FIG. 3). In mucosal samples, low titres of V-specific IgA were detected in the saliva at all time points analysed (FIG. 4A) with the highest titres seen at day 42 (FIG. 4B). Consistent with the superior performance of intranasally delivered V-OMVs for generating V-specific IgG antibodies, higher levels of V-specific IgA were seen in the saliva of animals immunised intranasally compared to those immunised via the oral route (FIG. 4A, C). The 25 µg dose of intranasally administered V-OMVs produced the highest titres of V-specific IgA in saliva (FIG. 4A), similar to serum V-specific IgG antibody responses (FIG. 3). By comparison, salivary gland V-specific IgA antibody titres at day 56 were equivalent in animals immunised with 12.5, 25 or 50 µg of antigen (FIG. 4C). The titre of V-specific IgA antibodies in the BAL were lower than that in both the saliva and salivary glands with no evidence of vaccine dose-level dependent responses as each dose of V-OMVs elicited similarly low levels of V-specific IgA (FIG. 4C).

Figure 4:
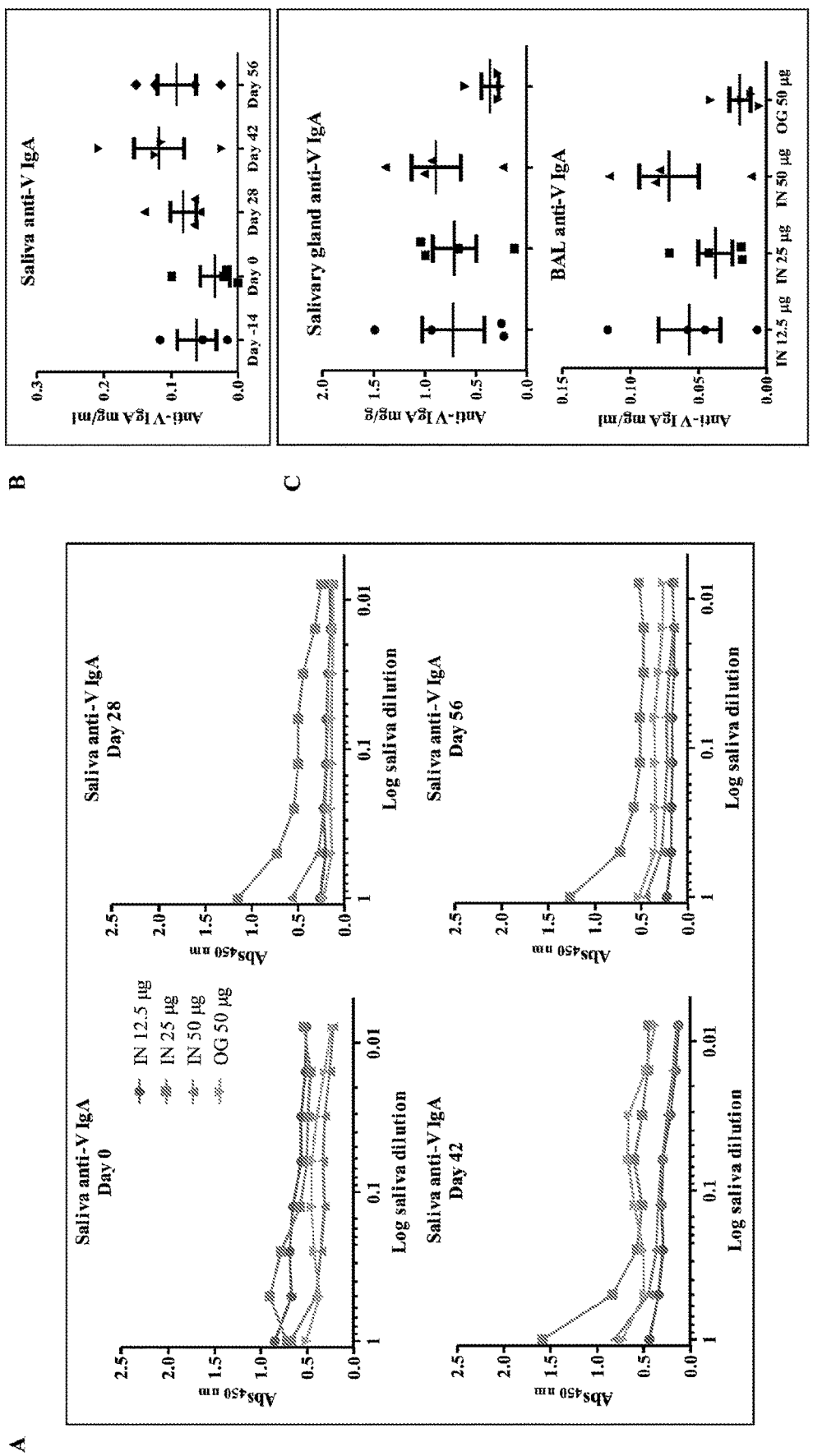
Figure 5:
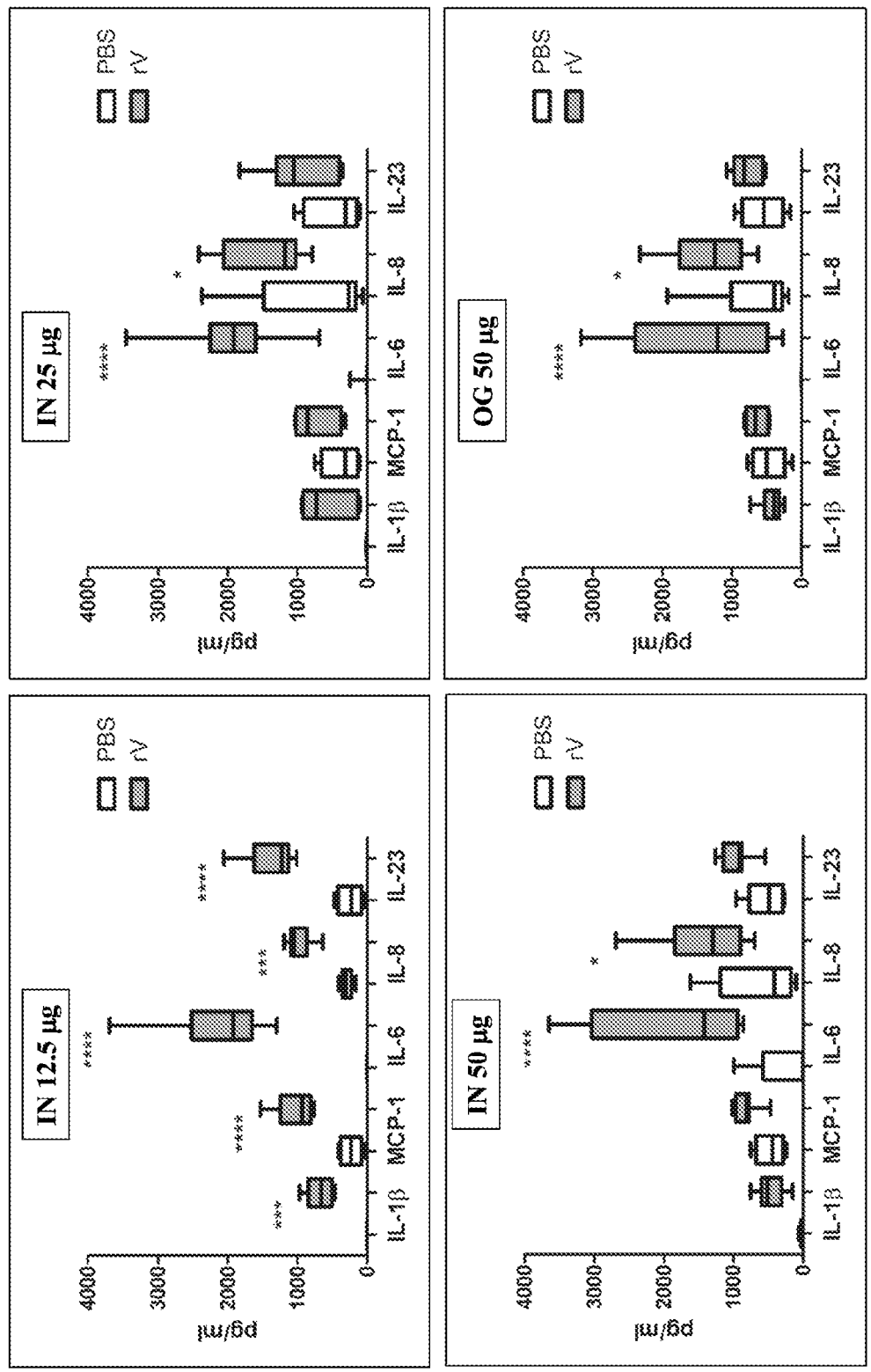

As an indicator of cell mediated immune responses to OMV vaccines we analysed the recall response of peripheral blood lymphocytes from animals immunised intranasally or orally with V-OMVs after re-stimulation with rV antigen in vitro. PBMCs from V-OMV immunised animals constitutively produced varying levels MCP-1, IL-6, IL-8 and/or IL-23 during culture in complete media alone (FIG. 5). In the presence of rV the levels of these cytokines were upregulated in all PBMC samples irrespective of the route or dose of V-OMVs used for immunisation. In addition, IL-1□ production which was absent in control, non-stimulated cultures, was induced by V antigen re-stimulation of PBMCs (FIG. 4). Other cytokines included in the analysis that were not detected in any PBMC sample or were present at levels below the detection limit of the assay (≤1.0 pg/ml) included IFN□, TNF□, IL-10, IL-12p70, IL-17A, and IL-18 (data not shown).

Safety of V-OMV Vaccines

Figure 6:
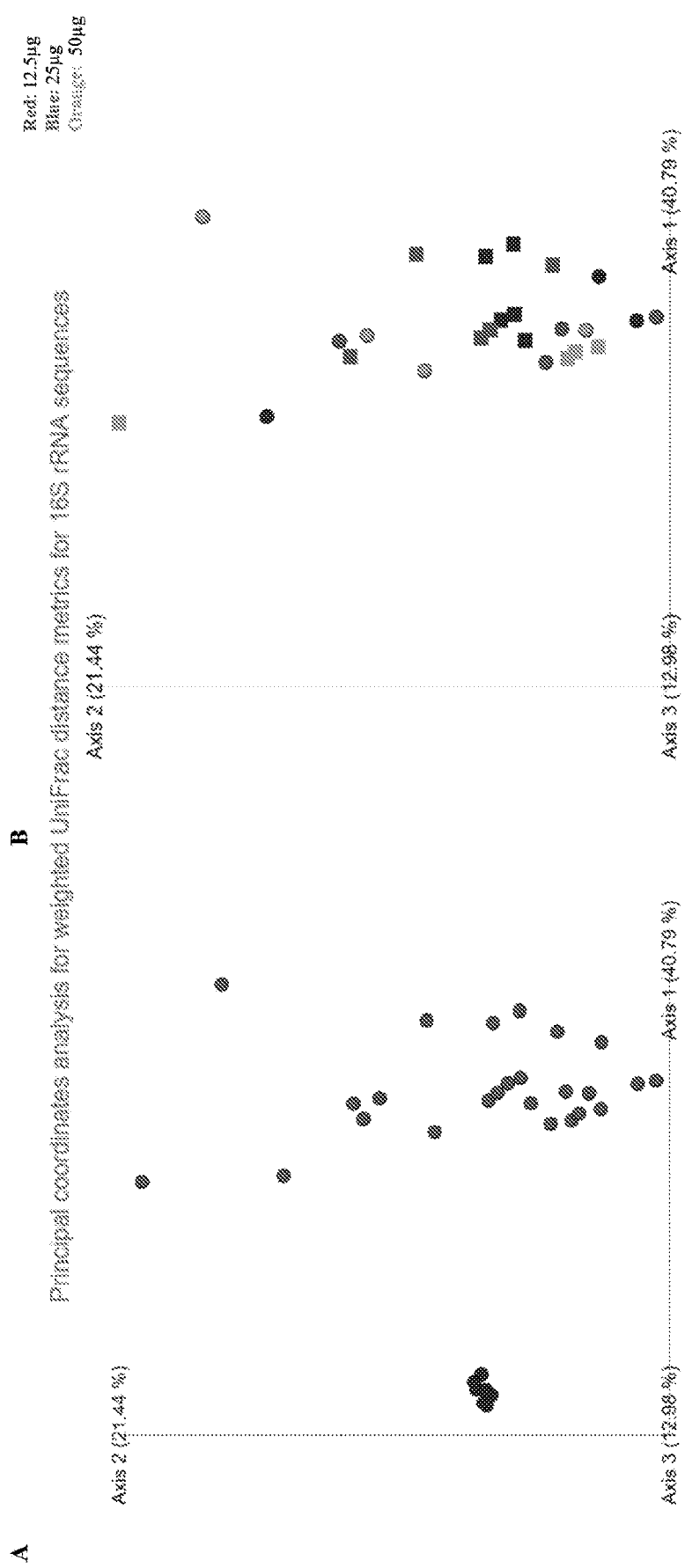

The biosafety evaluations of F-OMV and V-OMV vaccines were based on histopathology of tissue recovered at necropsy, and profiling resident microbe populations (microbiotas) of the GI- and respiratory tracts using 16S rRNA sequence-based community profiling of faecal- and nasal swab-derived DNA samples, respectively, pre- and post OMV immunisation (FIG. 6). Independent, blinded evaluation of various tissues (lung, spleen, liver, heart, lymph nodes, kidney, brain and regions of the GI-tract) at necropsy revealed no macroscopic signs of pathogenic infection or pathology.

Evidence of recent immune activation in the lymphoid tissues of the spleen and lymph nodes in a proportion of animals in each group of F1-OMV animals was seen; this comprised the presence of scattered secondary follicles with mitotic figures and apoptotic cells in the splenic white pulp and cortex of the lymph nodes. Microscopic examination of tissues from animals receiving the highest dose of V-OMVs (50 µg) identified regions of organised and enlarged lymphoid structures and follicles within the spleen and lungs in the absence of any infection or bacteria (data nor shown). Lympho-plasmacytic cell infiltrates were observed with some frequency in the mucosa of all parts of the GI tract; this is a common finding in non-human primates, and their presence likely reflects a low-grade, chronic-active gastritis/enteritis/colitis which may or may not be associated with clinical signs such as diarrhoea. Filamentous bacteria have been observed previously in the stomach of captive-bred macaques and *Balantidium* infection is a common, incidental finding in the caecum and colon of non-human primates, and is usually asymptomatic.

16S rRNA community profiling and PCA analysis of sequence data revealed little inter-individual differences in the faecal microbiota at baseline and prior to OMV vaccine immunisation (FIG. 6A). By contrast, there was considerable inter-individual variation in the nasal microbiotas of different animals at baseline (FIG. 6A). With the exception of one or two samples intranasal immunisation with V-OMVs did not noticeably alter the profiles at any vaccine dose (FIG. 6B) with the sequence data sets from pre- and post-immunised animals clustered closely together. These findings indicate that V-OMVs have no major impact on resident microbe (prokaryote) communities in the upper respiratory tract.

Functionality of OMV-Elicited IgG Antibodies

Two independent assays were used to assess the functionality of immune sera from OMV immunised animals and to determine their usefulness as potential immune correlates of protection in humans. The first assay used was a competitive (CE)-ELISA [1] that quantifies the ability of immune IgG to compete for binding to the *Y. pestis* V antigen with a monoclonal antibody (Mab 7.3) which can protect mice by passive transfer against plague infection [27]. The second assay is a novel bactericidal assay specifically developed for this study that assesses the level of antibody and complement killing of *Y. pestis* in serum samples using the *Y. pestis* reference strain CO92 as the target.

Serum samples collected at the study endpoint from representative animals within each of the different route of administration and dose-level groups were assayed for their ability to displace Mab 7.3 from binding to rV in vitro. The data are presented as a titration line for loss of binding of the mouse monoclonal antibody with increased concentration of test samples (see Materials and Methods) using as a reference, macaque immune sera obtained by parenteral immunization with rF1+ rV proteins (FIG. 7). The sera from animals intranasally administered V-OMVs at all doses inhibited to some extent the binding of Mab 7.3, which at the higher serum concentrations were comparable to the activity of the reference sera. Sera from animals immunized with 25 or 50 µg of V-OMVs contained the highest titre of competitive antibodies (FIG. 7). By comparison, sera from animals orally administered V-OMVs contained low or no antibodies capable of competing with Mab 7.3 for binding to V antigen.

The bactericidal assay provided a functional activity assessment of the 48 separate test groups of samples taken from immunised cynomolgus macaques. Throughout the assays conducted, the reference antisera (generated by immunising macaques with recombinant rF1 and rV) provided consistent dose-response bactericidal activity (BCA) behaviour (Table 1).

TABLE 1

Summary of serum antibody bactericidal assay outputs (ED50 in units of % serum†)

| Vaccine | Dose (µg) | Route | Day 0 | Day 28 | Day 42 | Day 56 |
|---|---|---|---|---|---|---|
| OMV-F1 | 50 | IN | 12.1 | 36.2 | 14.9 | >45 |
| OMV-V | 50 | IN | 0.6 | 5.5 | 0.8 | 14.9 |
| OMV-F1 | 25 | IN | 1.4 | 1.6 | 1.5 | 6.2 |
| OMV-V | 25 | IN | 1.9 | 0.5 | 15.3 | 13.7 |
| OMV-F1 | 12.5 | IN | >45 | 21.6 | >45 | 39.2 |
| OMV-V | 12.5 | IN | >45 | >45 | 20.9 | 22.5 |
| OMV-F1 | 50 | OG | >45 | 17.0 | 13.0 | >45 |
| OMV-V | 50 | OG | >45 | 1.8 | 6.3 | >45 |
| rF1 + rV Alhydrogel | 50 | IM | — | — | — | 10.7* |

IN = Intranasal administration;
OG = Orogastric administration;
IM = Intramuscular administration OMV-V = Bt OMVs containing *Y. pestis* V antigen;
OMV-F1 = Bt OMVs containing *Y. pestis* F1 antigen;
r = Recombinant protein produced in *E. coli*;
*= Average of six determinations;
— = not included in the study design. †The initial dilution of antibody in the assay was 45% hence the limit of the assay was nominally set at 45%. Sera found to have an ED50 below the limit of detection were assigned an ED50 of >45%

There was, however, a high background BCA in many groups of macaques at Day 0. Assessment of the health records of the study subjects did not uncover any unreported health conditions and no veterinary adverse health observations were made. Although screened and found to be clear of all know high consequence pathogens in primates, a routine rectal swab was able to identify *P. aeruginosa* in one study participant. Although this organism was not found to be causing disease or inducing any perceivable clinical sign of illness, it is possible that natural background immunity to such a commensal will cross-react with the type three secretion system (TTSS) components of *Y. pestis*. The conservation of the TTSS has been discussed and demonstrated in other studies [28-31]. Thus it is postulated that the high background BCA observed in some study animals is due to immunity to type three secretion elements of commensal bacteria present in the colony. This hypothesis is further supported by confirmation by ELISA that there was pre-existing immunity in some primates which cross-reacted with *Y. pestis* recombinant V antigen at Day 0 (FIG. 3). This immunity was confirmed in the CE-ELISA (FIG. 7).

Intranasal administration appeared to result in better serum bactericidal responses for both OMV-antigens. All groups immunised with V-OMVs appeared to demonstrate bactericidal activity during the study with the best response seen in the group immunised with 50 ug OMV-V intranasally at Day 42 post immunisation. For F1-OMV the data also suggests that intranasal immunisation dose of 25 µg is optimal. Whilst Day 56 BCA data (Table 1) suggests that there was some waning of immune functional activity in some groups, at Day 42 almost all groups (except the lowest intranasally dosed F1-OMV group) appeared to demonstrate functional immunity to *Y. pestis*.

Discussion

Using bacterial OMVs generated by the bioengineering of the major human commensal bacterium, Bt, we have successfully developed formulations of plague vaccine antigens suitable for direct delivery to mucosal sites including the respiratory tract, the site of pneumonic plague infection. Bt OMVs incorporating the V antigen were shown to generate robust humoral and cell mediated immune responses in both the upper and lower respiratory tract, and in the systemic circulation. Using two independent surrogate assays of protection, V-OMV elicited immune sera possessed properties important in immune protection, including the ability to kill *Y. pestis*.

Protection against pneumonic plague is the paramount requirement to prevent epidemic spread. An outbreak in Madagascar in 2017 caused in excess of 2,400 confirmed, probable and suspected cases of plague including more than 200 deaths, with the majority (~77%) of reported cases being clinically classified as pneumonic plague [32]. Foremost amongst the virulence factors secreted by *Y. pestis* are the F1 and V proteins that are pivotal in preventing phagocytosis and regulating type three secretion by the bacteria, respectively. When secreted from *Y. pestis*, V along with other *Yersinia* outer proteins (Yops) also plays roles in inhibiting cytokine production, platelet aggregation, and apoptosis of macrophages in addition to immune suppression [33]. When combined together as purified recombinant proteins V and F1 comprise a powerful candidate vaccine and are amenable to alternative formulations other than a liquid suspension with alum [34] or alhydrogel [3], which allows for mucosal or dual route [35] delivery.

Using a prime and single boost oral or nasal immunisation protocol, V-OMVs were effective at inducing antigen specific IgA in mucosal sites and IgG in the blood with intranasal delivery being the most effective route of administration, particularly for the induction of mucosal IgA responses. Intranasally delivered V-OMVs were also able to elicit cell mediated immune responses as evidenced by strong recall responses of PBMCs from immunised animals and the production of pro-inflammatory cytokines. The weaker immunogenicity of V-OMVs delivered via the oral route may reflect the more hostile environment of the GI-tract and the need to overcome significant physical (mechanical digestion), chemical (acidic/alkaline pH), biological (enzymes) and microbiological (the microbiota) barriers prior to accessing inductive immune sites in the lower GI-tract. However, despite these obstacles orally delivered V-OMVs were effective at generating functional antibodies, albeit at lower titres than that from animals immunised nasally with V-OMVs. At the earliest timepoint of serological analysis at 28 days post immunisation, systemic and mucosal antibody responses were established and increased over time. In comparison to recombinant protein based vaccines [35] OMV vaccine formulations may therefore be less effective at inducing rapid onset immune responses (within 14 days). If multiple doses are needed to accelerate the onset and increase the strength and duration of immune responses this is less of a problem for OMV vaccines that are non-invasive and more user-friendly than for injected recombinant protein vaccines. The effectiveness of *N. meningitidis*-based OMV vaccine formulations (MenBvac, VA-Mengoc-BC, PorA P1.6-24 and MeNZB) relies on a three or four dose immunisation regimen to provide protection in children and adults and control outbreaks of MenB disease [36]. The option of increasing the concentration of V antigen in OMV vaccine formulations is not supported by our data that shows that an intermediate dose of antigen (25 µg) intranasally performed as well as and if not better than a two-fold higher dose in terms of generating high tires of both mucosal and systemic antibodies.

The assessment of host immune responses in NHPs was complicated by a level of pre-existing immunity in some individuals prior to OMV immunisation. This "background" immunity was confirmed in three independent serum antibody assays conducted at three different laboratories and sites. Assessment of the health records of the study subjects in question did not uncover any unreported health conditions and no veterinary health observations were made. More extensive investigations identified that *Pseudomonas aeruginosa* was present in some sample swabs (SF unpublished observations). This however, was not accompanied by symptomatic infection and no veterinary interventions were required. Antibodies to the type three secretion system and the V antigen of *Y. pestis* are known to cross react with that of other pathogenic Gram negative bacteria including *P. aeruginosa* as well as *Vibrio* spp. and *Aeromonas* spp. that encode homologs of the *Yersinia* V antigen [28]. Whilst the presence of these bacterial species could not be confirmed in samples collected during the study, it is possible that they infected and were subsequently eliminated by the immune response they invoked in these animals at some time prior to this study and that V-OMV vaccines may have been assisted by such pre-existing cross-reactive immunity. It is noteworthy that this "background" immunity phenomena was not seen in every animal.

An important immune correlate of protection for a candidate vaccine is the ability to generate neutralising antibodies able to inhibit bacterial killing of host target cells and/or that are cytotoxic and can actively kill the bacteria [3]. Using a novel *Y. pestis* bactericidal assay, immune sera from F1- and V-OMV immunised NHPs were shown to kill bacteria via antibody-dependent cell-mediated cytotoxicity (ADCC) with intranasally administered V-OMVs being particularly effective at generating high titres of bactericidal antibodies. Consistent with the ability of V-OMVs to generate neutralising antibodies, immune sera from V-OMV immunised animals contained V-specific antibodies reactive with epitopes of the V antigen bound by a monoclonal anti-V antibody (Mab7.3) that protects mice by passive transfer against plague infection [27]. The bactericidal activity of sera from F1-OMV immunised animals is perhaps surprising in view of their weaker immunogenicity and the low levels of antigen specific antibodies they generated compared to V-OMV vaccines (FIG. 2). The low levels of F1 expression in Bt, which required sensitive LC-MS techniques for detection, may be a consequence of inherent differences in the translational machinery and requirements for efficient synthesis and/or in secretion sequences used to target newly synthesised proteins to the periplasm and OMVs in *Yersinia* versus *Bacteroides* spp. In addition, the inability of Bt to efficiently synthesise proteins encoded within the caf1 operon, such as caf1M which encodes a protein that appears to act as a chaperone for F1 with a role in its post-translational folding and secretion [37], could also compromise Bt expression of F1. The inability to detect F1 in F1-OMV lysates using various antibodies in immunoblotting protocols may also be indicative of low levels of expression or the protein not being expressed in its native form, or expression of altered structural determinants resulting in the loss of immune epitopes through expression in Bt and OMVs.

Studies carried out in various animal models including NHPs [32, 16, 33-36, 37] indicate that although neutralising antibodies provides protection against exposure, the development of cell-mediated immunity is essential for protection and clearance of bacteria from the host. Studies using mice with targeted mutations that disrupt Th1 or Th2 CD4 T cells responses have shown that Th1 driven cell mediated immune responses are particularly important in protecting against plague [38]. The ability of the V protein to upregulate IL-10 production which downregulates the generation of pro-inflammatory cytokines such as $TNF\alpha$ and $IFN\gamma$ is a key mechanism of virulence and immunosuppression, contributing to the disruption of a balanced Th1/Th2 response that alongside specific antibodies appears to be optimal for protection [3]. In this context the recall response of lymphocytes from V-OMV immunized animals that is characterised by the secretion of various pro-inflammatory cytokines is significant and of predicted benefit in mobilising (MCP-1, IL-8) and activating (IL-1$\beta$, IL-6, IL-23) components of cell-mediated immune responses in response to plague infection in immunized animals.

In summary, the key findings from our study are that Bt OMVs can stably express plague antigens, and in particular the V antigen, in the correct, immunogenic form and that these engineered OMV vaccine formulations elicit specific immune and antibody responses both in the serum and at mucosal surfaces, including the generation of antibodies able to kill plague bacteria. Our results also highlight key advantages our Bt OMV vaccine technology offers over current plague vaccines in terms of technology and/or approach. First, OMV vaccine delivery via oral or nasal administration allows for needle-free, multi-dose delivery that would enable mass vaccination programs in challenging environments and at relatively low cost. Advantageously, this route of immunisation targets primary sites of mucosal infection as compared to injectable whole cell or subunit vaccines. Second, compared to subunit or whole cell vaccines the manufacture and re-formulation of OMV vaccines is quicker and can be achieved using readily accessible, relatively inexpensive technology that has been commercially validated in the production of licensed MenB OMV vaccines in current use [39]. Third, patient acceptance is anticipated to be high, requiring out of clinic administration as compared to injection based vaccines. Fourth, OMVs have intrinsic adjuvanticity and the ability to activate both the innate and adaptive arms of the immune system [21, 22] compared to the requirement for chemical adjuvants such as alum to improve immunogenicity of subunit vaccines. Fifth, OMV vaccines are acellular and non-infectious increasing their safety compared to live attenuated or killed whole cell vaccines. Finally, OMVs are stable for ultra-long periods in liquid and lyophilised form [40] and for several weeks in solution across a wide range of temperatures including 40° C. allowing distribution to the point of need without cold chain or cold storage, which is particularly advantageous for use in tropical and low income settings.

Materials and Methods

Bacteria, Media, Growth Conditions and Transformations

*E. coli* strains were grown in Luria-Bertani medium at 37° C. Bt strain VPI-5482 and derivative strains were grown under anaerobic conditions at 37° C. in BHI medium (Oxoid, UK) supplemented with 0.001% haemin (BHIH) or, with 0.00005% haemin for OMV preparations. Antibiotics were added as selective agents when appropriate: ampicillin 200 µg/ml and erythromycin 5 µg/ml. The *E. coli* strain J53/R751 was supplemented with trimethoprim 200 µg/ml when grown for 18 h. *E. coli* GC10 was transformed by electroporation using a Gene Pulser II (Bio-Rad, UK). Plasmids were mobilized from *E. coli* into Bt following a triparental filter mating protocol [23] using the helper strain J53/R751. *Y. pestis* strain CO92 (biovar Orientalis, NR641, BEI Repositories) was supplied by the Biodefence and Emerging Infections (BEI) Research Repository (USA) in accordance with International Export and Import Regulatory Requirements. The organism was stored and handled in accordance with US Biological Select Agent or Toxin requirements and was grown using the conditions described previously [24].

Construction of *Yersinia pestis* F1- and V1-Antigen Expression Vectors

A synthetic gene construct of 1043 bp encoding the V antigen and a synthetic operon construct of 3826 bp encoding caf1M, caf1A and caf1 genes of the caf1 operon that generates the F1 protein were N-terminally fused to the OmpA signal peptide of Bt to create a construct in silico with their codon usage being optimised for expression in the same species. Signal peptide prediction was obtained by SignalP at http://www.cbs.dtu.dk/services/SignalP/. During the design of the synthetic constructs the unique *Bacteroides* ribosomal binding site [25] required for efficient expression in *Bacteroides* was accounted for. The resulting gene cassettes were obtained through gene synthesis and subsequently cloned into the *E. coli* plasmid pEX-A2 and pEX-K4 to (Eurofins, Germany), respectively. The cassettes contain BspHI and EcoRI restriction sites at their 5' and 3' ends, respectively, allowing for the translational fusion of the encoded gene to the start codon in the *Bacteroides* expression vector pGH090 [25]. The genes encoding V1 or F1 were excised from the pEX derivatives using BspHI and EcoRI and ligated into the NcoI/EcoRI-restricted pGH090 expression vector, resulting in pGH179 and pGH180 respectively. Finally, the sequence integrity of the cloned fragments was verified through sequencing.

Nanoparticle Analysis

Videos were generated using a Nanosight nanoparticle instrument (NanoSight Ltd, Malvern, USA) to count OMV numbers in each OMV sample. Simultaneous measurement of the mean squared displacement of each OMV tracked, the particle diffusion coefficient ($D_t$) and hence sphere equivalent hydrodynamic radius ($r_h$) were determined using the Stokes-Einstein equation, $$D_t = \frac{k_B T}{6\pi\eta r_h},$$

where $k_B$ is Boltzmann's constant, T is temperature and η is solvent viscosity.

Immunoblotting

OMV-V extracts were added to SDS-PAGE loading buffer (NuPage) containing dithiothreitol (Invitrogen). Approximately 7 μg of OMV-V were loaded onto 12% precast Tris-Glycine gels (Novex) and separated by electrophoresis at 180 volts for 40 min. Gels were transferred onto a polyvinylidene difluoride membrane at 25 volts over 2 h in a solution containing Tris-glycine transfer buffer (Novex). The membrane was blocked with 10% BSA in TBS (50 mM Tris-HCl, 150 mM NaCl, pH 7.5)-Tween (0.05%) for 30 min at 20° C. Blocking solution was then discarded and the membrane incubated for 16 h at 4° C. in a 1:1000 dilution of a primary mouse anti-V antibody (Dstl, UK) in TBS-Tween with 5% BSA. After washing with TBS-Tween 3 times, membranes were incubated 1 h at 20° C. in 5% BSA in TBS-Tween with a 1:1000 dilution of HRP-conjugated goat anti rabbit IgG (ThermoFisher). After 3 washes with TBS-Tween, SuperSignal West Pico chemiluminescent Substrate (ThermoFisher) was used to detect bound antibody. The detection of F1 in Bt OMV preparations was determined by liquid chromatography and mass spectrometry-(LC-MS) based proteomics (Proteomics Facility, Univ. Bristol, UK).

Cytokine Analysis

Frozen PBMCs obtained from whole blood by density gradient centrifugation over Ficoll-Paque Plus (Amersham Biosciences, Chalfont St. Giles, UK) were thawed, washed twice with RPMI media containing 10% FBS, 2 mM glutamine and 100 U/ml penicillin/streptomycin and adjusted to a concentration of $5\times10^5$ cells/ml. Aliquots of $10^6$ cells were plated into individual U wells of 96 well plates and incubated in triplicate with media alone or media containing 15 μg/ml rV protein for 72 h at 37° C. in an incubator with 5% $CO_2$. Control cultures contained media alone. Conditioned media was then harvested and cytokine content determined using a bead-based multiplex assay and BD LSRFortessa flow cytometer (BD Biosciences, San Jose, Calif.) according to manufacturer's instructions (BioLegend, San Diego, Calif.).

Antibody ELISA 96 well Nunc-Immuno Microwell plates (Thermo Scientific) were coated with 15 μg/ml of *Y. pestis* V (BG032/VDJPE1) or F (BG032/FD5Pst2) recombinant proteins (Dstl, UK) in ELISA-coating buffer (0.1 M NaHCO3) and incubated for 16 h at 4° C. After washing 3 times with ELISA wash buffer (PBS with 1:2000 Tween-20), plates were blocked for 3 h with blocking buffer (PBS with 2% BSA) at 20° C. with gentle agitation. Serum, saliva, salivary gland and BAL samples were added in dilutions ranging from 1 to 163,840 and the plates were incubated 16 h at 4° C. After 6 washes with ELISA wash buffer, 50 μl of 1:10000 goat anti-monkey IgG peroxidase conjugated (Sigma: A2054-1 ml) or 1:10000 goat anti-monkey IgA-HRP antibody (Sigma: SAB3700759) were added and plates were incubated for 1 h at 20° C. with gentle agitation. Plates were then washed 6 times with ELISA wash buffer and incubated with 100 μl of TMB High Sensitivity Substrate Solution (BioLegend) for 20 min at 20° C., in the dark. The reaction was stopped by adding 50 μl of 2 N $H_2SO_4$. The plates were analysed in a microplate reader at $Abs_{450\ nm}$. Absolute amounts of IgG and IgA antibodies in serum and mucosal samples respectively, were determined using a modified ELISA incorporating a range of concentrations of purified monkey IgG (Bio Rad) and IgA (Life Diagnostics, Inc) and the protocol and reagents described above to generate standard curves from which IgG and IgA concentrations of individual animals were determined.

Bactericidal Assay

This prototype assay was developed in a series of experiments which optimised incubation times, heat treatment and complement concentration using a standard anti-rF+rV antiserum generated in cynomolgus macaques. Human volunteer and baby rabbit complement (Pellfreeze) were found to be similar in sensitivity to antibody directed bactericidal activity against *Y. pestis* CO92. Briefly, heat-treated primate sera were incubated with live *Y. pestis* bacteria in the presence of 25% v/v rabbit complement for X hours with orbital agitation on a 96 well plate shaker. After this incubation, the mixture was plated into blood agar and permitted to be absorbed into the agar. The plates were then incubated at 37° C. for two days before manual enumeration was conducted to assess relative viability. The number of bacteria counted for each test serum antiserum was used to calculate the reduction in counts obtained from plate spread with the no-antibody, complement control. The dose of test serum (expressed as percentage (v/v) of serum) required to kill 50% of live *Y. pestis* CO92 was calculated by interpolation of the dose response curved for sample. Each assessment was conducted in duplicate. Bactericidal antibody assessment assays were conducted at PHE on samples taken on each of the four sample days with serum pools from each of the 12 vaccine group. In all studies, the reference standard anti-rV plus anti-rF1 primate serum was also assessed as a means of comparison and measure of reproducibility. In all studies, this standard antiserum performed in a reproducible manner. All controls (including the complement only no antibody control) were assessed and found to be performing as expected.

Competitive ELISA

The detection of antibodies in immune sera from V-OMV immunized animals able to compete for binding with a monoclonal antibody (Mab7.3) to recombinant V protein was determined in a competitive ELISA (CE-ELISA) assay as previously described [1]. Briefly, rV antigen was coated to 96-well microtitre plates (Dynex) at 5 μg/ml in 0.05 ml PBS (16-18 h, 4° C.). After washing, in PBS with 0.02% Tween 20, plates were blocked with 0.2 ml 5% w/v skimmed milk powder in PBS (37° C., 1 h). After further washing, 0.05 ml Mab7.3 (1:32,000 in 1% w/v skimmed milk powder in PBS) was added to each well (equivalent to 80 ng/well) and plates were incubated at 4° C. for 16 h. Normal NHP serum, also diluted to 1:32,000, was added to negative control wells (0.05 ml per well). Plates were then washed prior to adding the test serum at a dilution of 1:10 in 1% w/v skimmed milk powder in PBS. A positive control, comprising a reference serum created by pooling equal aliquots of sera from 4 macaques previously parenterally immunized with rF1+ rV antigens and subsequently surviving challenge with *Y. pestis,* was included. Test and control serum samples were assayed in duplicate. Plates were incubated (1 h, 37° C.) prior to washing and addition of HRP-goat anti-mouse IgG (Serotec; 1:2000 in PBS) followed by incubation (37° C., 1 h). Plates were washed prior to addition of ABTS substrate (Sigma) with subsequent reading of absorbance at 414 nm. The $OD_{414\ nm}$ determined for each test and the reference serum was adjusted by subtraction of the $OD_{414\ nm}$ determined for the appropriate control serum. The data were calculated from a titration curve for loss of binding of the mouse antibody, with increased concentration of human serum.

Animal Experiments

All animal experiments were conducted in full accordance with the Animal Scientific Procedures Act 1986 under UK Home Office approval. Animal experiments were performed using cynomolgus macaques (Macaca fascicularis) that were bred and maintained in animal facilities at PHE, Porton, UK. All animals were free of herpes B-virus, TB, SIV and STLV and were inspected by the Named Veterinary Surgeon prior to entry into the study. Animals were housed in their existing social groups in pens which are designed in accordance with the requirements of the United Kingdom Home Office Code of Practice for the Housing and Care of Animals Bred, Supplied or Used for Scientific Purposes, December 2014.

Generation of Standard Reference Antisera.

In order to enable development of a functional biological assay of relevance to these studies, antisera to F1 and V were generated by immunising two cynomolgus macaques with either recombinant F1 (Batch BG032\FD5Pst2, Dstl) or recombinant V (batch BG032\VDJPE1, Dstl) antigen formulated into Alhydrogel adjuvant. Both vaccines were prepared and supplied to PHE by Dstl. Two primates (one male, one female) were immunised with either vaccine on two occasions 3 weeks apart. The dose on each vaccination occasion was 50 μg injected intramuscularly in a 250 μl volume. Once an immune response was confirmed to have been induced via ELISA, the subjects were humanely euthanised in accordance with a UK Home Office project license and schedule 1 guidance. The sera were collected after centrifugation of serum separation tubes which had permitted the blood to clot. Serum aliquots were created and frozen at below −20° C. until required. Stool samples are also collected for reference purposes into OMNIgene GUT OMR-200 tubes.

OMV Vaccines and Vaccination

First, reference anti-V and -F1 antisera were generated by immunising cynomolgus macaque (n=4 of equal sex) intramuscularly with recombinant purified F1 and V antigens (50 μg ea.) in a total volume of 250 μl of 20% (v/v) alhydrogel. A booster immunisation was given at day 28 with immune sera obtained at the study end point at day 56. Prior to OMV vaccine immunisations the immune status for each animal with regard to *Y. pestis* antigens were assessed at 14 and 0 days before immunisation. For OMV-V/F1 vaccine studies, groups of animals (n=4/grp of equal sex) were immunised with OMV-V or OMV-F1 vaccine formulations containing 12.5, 25 or 50□ g of V/F1 protein via the intranasal route or, with 50 μg of V/F1 protein via the oral route in a total volume of 1 ml PBS. Twenty-eight days later all animals received a booster immunisation via the same route of administration. Blood, stool, saliva and rectal and nasal swab samples were collected at day −14, 0, 28, 42 and at the study end point of 56 days with body weight, temperature, axillary and inguinal lymph node scores and haemoglobin concentration determined at each sampling timepoint. At necropsy lung, spleen, liver, heart, lymph nodes, kidney, brain, stomach and intestine were collected for histopathology. The tissues were examined by light microscopy and evaluated subjectively by a pathologist, blinded to the treatments and groups in order to prevent bias.

Statistical Analysis

CE-ELISA data were analysed using Graph Pad Prism software v.6 and expressed as mean±SEM. Statistical comparisons were made using one-way ANOVA or unpaired t-test. The survival data were expressed as Kaplan-Meier survival curves and statistical significance was determined by Log-rank test. $P<0.05$ was considered statistically significant.

Referring now to the influenza vaccine and Bioengineering human gut commensal bacteria derived outer membrane vesicles for the delivery to of biologics to the gastrointestinal and respiratory tract more generally; we have undertaken a proof-of-principle study to determine the suitability of using OMVs produced by *Bacteroides thetaiotaomicron* (Bt), a prominent member of the intestinal microbiota of all animals, to deliver bacteria-, virus- and human-derived proteins to the respiratory and GI-tract to protect against infection and tissue inflammation and injury using mouse models of respiratory influenza infection and acute intestinal colitis. Our findings presented here demonstrate the ability to express and package within or on the outer membrane of Bt OMVs both bacteria and virus derived vaccine antigens in a form capable of eliciting antigen specific immune and antibody responses in mucosal tissues and systemically. Furthermore, immunisation with OMVs containing influenza virus vaccine antigens induced heterotypic protection in mice to a 10-fold lethal dose of influenza A virus (IAV). We also show that OMVs can stably express human therapeutic proteins as exemplified by human keratinocyte growth factor-2 (KGF-2) which when delivered orally reduces disease severity and promotes intestinal epithelial repair and restitution in animals administered colitis-inducing dextran sodium sulphate (DSS). Together our data provides evidence of the utility and effectiveness of using Bt OMVs as a mucosal biologics and drug delivery platform technology.

Materials and Methods

Bacteria Strains, Media and Culture

*Bacteroides thetaiotaomicron* (Bt) and derivate strains (Table 102) were grown under anaerobic conditions at 37° C. in BHI medium (Oxoid) supplemented with 0.001% haemin (Sigma-Aldrich, St Louis, USA) (BHIH). Antibiotic-resistance markers in *B. thetaiotaomicron* were selected using erythromycin (5 μg/ml) and tetracycline (1 μg/ml). *E. coli* strains were grown in Luria-Bertani (LB) medium at 37° C. with ampicillin 100 μg/ml or trimethoprim 200 μg/ml for J53 (pR751) strain. *Lactococcus lactis* UKLc10 and derivative strains were grown in M17 medium (Oxoid) supplemented with 5 g/l glucose at 30° C. Antibiotics were added as selective agents when appropriate: ampicillin 200 μg/ml, erythromycin 5 μg/ml and chloramphenicol 10 μg/ml. The *E. coli* strain J53/R751 was supplemented with trimethoprim 200 μg/ml when grown for 18 h. *E. coli* GC10 and *L. lactis* UKLc10 were transformed by electroporation using a Gene Pulser II (Bio-Rad, UK). For constructs relating to pUK200, the host strain *L. lactis* UKLc10 was used. Other construction of plasmids described below were performed using *E. coli* GC10 as host. Plasmids were mobilized from the *E. coli* into Bt following a triparental filter mating protocol [19] using the helper strain J53/R751. Primers used in this study are detailed in Table 102.

Construction of a Bt_3852 Deletion Mutant

A XXX bp chromosomal DNA fragment upstream from Bt_3852 including the first 18 nucleotides of its 5'-end region was amplified by PCR using the primer pair f-5'ompA_SphI, r-5'ompA_SalI. This product was then cloned into the SpHI/SalI sites of the *E. coli-Bacteroides* suicide shuttle vector pGH014 [20]. A XXX bp chromosomal DNA fragment downstream from BT_3852, including the last 46 nucleotides of the 3'-end region, was amplified by PCR using the primer pair f-3'ompA_BamHI, r-3'ompA_SacI and was cloned into the BamHI/SacI sites of the pGH014-based plasmid. The resulting plasmid containing the ΔBT_3852::tetQ construct, was mobilized from *E. coli* GC10 into Bt by triparental filter mating [19], using *E. coli* HB101 (pRK2013) as the helper strain. Transconjugants were selected on BHI-haemin agar containing gentamicin (200 mg/L) and tetracycline (1 mg/L). Determination of susceptibility to either tetracycline or erythromycin was carried out to identify recombinants that were tetracycline resistant and erythromycin susceptible after re-streaking transconjugant bacteria on LB-agar containing tetracycline or both antibiotics. PCR analysis and sequencing were used to confirm the allelic exchange. A transconjugant, GH290, containing the ΔBT_3852::tetQ construct inserted into the Bt chromosome was selected for further studies.

Generation of Recombinant Bt Strains

Bt *Salmonella* OmpA/SseB: The *Bacteroides* expression vector pGH090 [21] was first digested with the restriction enzyme NdeI to remove this site by Klenow treatment and to create a blunt-ended fragment that was then religated. A sequence containing the 90 bp of the Bt_3852 gene 5' end (encoding a major outer membrane protein, OmpA) corresponding to the signal peptide sequence (SpOmpA) of the protein obtained from the microbial genome database (http://mbgd.genome.ad.jp/) was used to design the complementary oligonucleotide pair SPBTOmpA_fwd and SPBTOmpA_rev. After annealing of the oligonucleotides following a protocol provided by Merck the resulting double-strand DNA contained EcoRI and SpHI 5' overhangs at each end. This linker was cloned into the EcoRI/SpHI sites of the NdeI deleted version of pGH090, resulting in pGH202 plasmid. The 1100 bp ompA and the XXX bp sseB coding region from *S. typhimurium* were amplified by PCR from genomic DNA of strain SL1344 using the primer pairs OmpAST_fwd, OmpAST_rev and SseB_fwd, SseB_fwd, respectively. The resulting fragments were digested with NdeI and EcoRI and cloned into NdeI/EcoRI-digested pGH202, yielding plasmids pGH182 and pGH183, respectively. The later plasmid was then transformed into *E. coli* competent cells (GC10) through electroporation using a Gene Pulser II (Bio-Rad, UK). Successful cloning was checked by sequencing. The plasmid was mobilized from *E. coli* to Bt through a triparental mating procedure [19], together with *E. coli* J53 (pR751) and the correct structure of Bt carrying pGH182 (GH484) was confirmed by sequencing.

Bt IAV: A 635 bp synthetic gene construct encoding a synthetic influenza (H5F; from IAV strain H5N1 (VN/04: A/VietNam/1203/04)) pre-fusion headless HA mini-stem N-terminally fused to the OmpA signal peptide of Bt was created in silico and its codon usage was optimised for expression in the same species. The resulting gene cassette was obtained through gene synthesis and subsequently cloned into the *E. coli* plasmid pEX-K168 (Eurofins, Germany). The cassette contains BspHI and EcoRI restriction sites at its 5' and 3' ends, respectively, allowing for the translational fusion of the gene to the start codon in the *Bacteroides* expression vector pGH090 [21]. The gene was excised from pEX-K168 using BspHI and EcoRI and ligated into the NcoI/EcoRI-restricted pGH090 expression vector, resulting in pGH184. Finally the sequence integrity of the cloned fragment was verified through sequencing.

Bt KGF-2: A 581 bp synthetic gene construct encoding the human fibroblast growth factor-10/keratinocyte growth factor-2 (KGF-2) N-terminally fused to the OmpA signal peptide of Bt was created in silico and its codon usage was optimised for expression in the same species. The resulting gene cassette was obtained through gene synthesis and subsequently cloned into the *E. coli* plasmid pEX-A2 (Eurofins, Germany) as described for the IAV constructs. The final expression vector was pGH173 with the sequence integrity of the cloned fragment verified by sequencing.

Expression and Purification of Recombinant StOmpA and StSseB

StOmpA was cloned into His6.tag expression vector pET-15b (Novagen). Briefly, PCR fragments incorporating the coding sequences of ompA and sseB genes were cloned into the NdeI/XhoI restriction sites of pET-15b and the resulting plasmids pGH165 and . . . ) transformed into Rosetta2 (DE3)pLysS cells yielding strains EcOmpA and EcSseB (Table 102). EcOmpA/SseB cultures were induced at $OD_{600\ nm}$ 0.6 by adding 1 mM IPTG for 5 h after which cells were harvested by centrifugation (5500 g for 20 min). The pellet was kept at −20° C. until further use. StOmpA and StSseB proteins were purified under native conditions using protocols adapted from QIAexpress Ni-NTA Fast Start Handbook (Qiagen) with the amount of protein recovered determined using the Bio-Rad Protein Assay.

OMV Isolation and Characterisation

OMVs were isolated following a method adapted from Stentz et al [20]. Briefly, cultures (500 mL) of Bt were centrifuged at 5500 g for 45 min at 4° C. and the supernatants filtered through 0.22 μm pore-size polyethersulfone (PES) membranes (Sartorius, Goettingen, Germany) to remove debris and cells. Supernatants were concentrated by ultrafiltration (100 kDa molecular weight cut-off, Vivaspin 50R, Sartorius), the retentate was rinsed once with 500 mL of PBS (pH 7.4) and concentrated to 1 mL (approx. 700 μg/ml total protein). The final OMV suspension were filter sterilized with a 0.22 μm filter. The protein content of the final OMV suspensions was determined using the Bio-Rad Protein Assay.

The distribution of heterologous proteins within Bt OMVs was established in a Proteinase K accessibility/protection assay [20]. Briefly, a suspension of 250 μg of OMVs in 0.1 M phosphate/1 mM EDTA buffer (pH 7.0) was incubated for 1 h at 37° C. in the presence of 100 mg/L proteinase K (Sigma-Aldrich). Proteinase K activity was stopped by addition of 1 mM phenylmethanesulfonyl fluoride (PMSF) and samples analysed by immunoblotting. The SseB content of Bt OMVs was determined by targeted proteomics at the University Bristol, UK, Proteomics Facility.

Nanoparticle Analysis

Videos were generated using a Nanosight nanoparticle instrument (NanoSight Ltd, Malvern, USA) to count OMV numbers in each OMV sample. Simultaneous measurement of the mean squared displacement of each OMV tracked, the particle diffusion coefficient ($D_t$) and hence sphere equivalent hydrodynamic radius ($r_h$) were determined using the Stokes-Einstein equation, $$D_t = \frac{k_B T}{6\pi\eta r_h},$$

where $k_B$ is Boltzmann's constant, T is temperature and η is solvent viscosity.

Immunoblotting

Bt cell and OMV extracts were obtained by sonication and the supernatants added to SDS Page loading buffer (NuPage) containing dithiothreitol (Invitrogen). Approximately 7 µg of the total protein were loaded onto 12% precast Tris-Glycine gels (Novex) and separated by electrophoresis at 180 volts for 40 min. The gel was then transferred onto a Polyvinylidene difluoride (PVDF) membrane at 25 volts over 2 h in a solution containing Tris-GLycine Transfer Buffer (Novex). The membrane was blocked with 10% BSA in TBS-Tween (TBS (50 mM Tris-HCl; 150 mM NaCl; pH 7.5) with 0.05% Tween) for 30 min shaking at 20° C. Blocking solution was then discarded and the membrane incubated for 16-18 h at 4° C. in TBS-Tween with 5% BSA containing primary antibody (anti-*Salmonella* OmpA [Antibody Research Corporation], -KGF-2 [ . . . ] or -IAV HA[ . . . ] antibodies). After washing with TBS-Tween, membranes were incubated in 5% BSA in TBS-Tween containing HRP-conjugated goat anti rabbit IgG (1:1000 dilution, ThermoFisher) for 1 h at 20° C. After 3 washes with TBS-Tween, SuperSignal West Pico chemiluminescent Substrate (ThermoFisher) was used to detect bound antibody.

Mammalian Cell Culture

The human colonic epithelial cell line Caco-2 (ECACC 86010202) was cultured at 37° C. and 5% CO2 in Dulbecco's Modified Eagle Medium (DMEM) with 4.5 g/L glucose and L-glutamine (Lonza, Switzerland) supplemented with 5% foetal bovine serum (FBS, Lonza, Switzerland).

Epithelial Cell Scratch Assay

Caco-2 cells were grown in T25 flasks until they reached 90% confluency. Cells were digested using trypsin EDTA (200 mg/L, 170,000 U Trypsin/L, Lonza, Switzerland) and seeded onto 8-well µ-slides (Ibidi, Germany). Cells were grown until they formed a 90% confluent monolayer and then serum-starved for 8 h. A scratch was performed on the monolayer using a sterile tip and cells were washed with PBS to remove cell debris. The remaining cells were incubated for 72 h in 1% FBS medium supplemented with heparin (300 µg/mL grade I-A, >180 USP units/ml; Sigma-Aldrich, USA) in the presence of PBS, naïve OMVs, KGF-2 OMVs or recombinant KGF-2 (500 ng/mL, PeproTech, USA). Wound healing was monitored by taking images immediately after scratching, representing a time 0 control, and every 24 hours using Invertoskop ID03 inverted microscope (Carl Zeiss, Germany) and a Sony Xperia Z5 compact digital camera (Sony, Japan). The measurements of the recovered scratch area (pixel$^2$) at each time point were analysed using ImageJ software (USA). The experiment was performed in triplicate.

Animal Experiments

Animal experiments were performed using 6 to 8 week old C57BL/6 single sex mice that were bred and maintained in animal facilities at the University of East Anglia (UK) and University of Liverpool. Mice were housed in individually ventilated cages and exposed to a 12 h light/dark cycle with free access to a standard laboratory chow diet. Animal experiments were conducted in full accordance with the Animal Scientific Procedures Act 1986 under UK Home Office approval.

Acute Colitis

The dextran sulphate sodium (DSS) induced mouse model of acute colitis was used to test the therapeutic potential of KGF-containing OMVs. Groups of male C57BL/6 mice of 8-11 weeks of age were divided into six groups (n=5-10/grp) administered either PBS, wild type OMVs, KGF-OMVs, DSS alone, DSS+wild type OMVs or, DSS+KGF-OMVs for 7 days. Experimental colitis was induced in the selected groups of mice by administration of 2.5% w/v DSS (36,000-50,000 MW, MP Biomedicals, USA) in drinking water ad libitum for 7 days. The other groups of mice received fresh water alone throughout for the duration of the experiment. PBS and OMVs were administered by oral gavage (100 µL) on days 1, 3 and 5 and on day 7 mice were euthanized. Fresh faecal pellets were collected daily by placing individual mice in an empty cage without bedding material for 5-15 min. The extent of colitis was evaluated using a disease activity index (Table S1) made up of determined from daily body weight, stool consistency and rectal bleeding assessments. At autopsy the colon was aseptically extracted and photographed, and the contents collected in sterile vials and stored at −80° C. The colon length was measured, and representative samples (0.5 cm length) were taken from the distal region for histology by fixing in 10% neutral buffered formalin and embedding in paraffin. Tissue sections (5 µm) were prepared from each block, stained with 0.5% Mayer's hemalum and Y-eosin solution (H&E, Merck, Germany), and with Alcian blue (Sigma-Aldrich, USA) to visualise goblet cells. Sections were observed under a DMI 3000B microscope at 40× magnification (Leica, Germany) and assessed in a blinded fashion. The histological changes were scored (Table S2) and goblet cells enumerated using ImageJ software (USA).

OMV Vaccines and Vaccination

For oral immunisation with *Salmonella* OMV vaccine formulations, 100 µl of StOmpA-OMVs in PBS were administered by oral gavage Booster immunisations were given 1 and 2 months later. A control group of mice were immunised via oral gavage with native OMVs. Prior to each immunization food was removed for approximately 4 h to decrease stomach acidity. An additional control group of animals were immunised with StOmpA-OMVs via the intraperitoneal route. For intranasal immunisation with *Salmonella* and influenza virus OMV vaccine formulations, mice were anaesthetized then intranasally dosed with either StOmpA OMVs, StSseB OMVs, H5F OMVs, native OMVs or PBS (n=5-10 ea.) and 7 and 14 days later received booster immunizations. For infectious challenge with *Salmonella*, StOmpA-OMV orally or ip immunised mice were orally administered 10$^8$ CFU of *S. typhimurium* SL1344 on day 28 and 5 days later the bacterial load in different tissues was determined. For infectious challenge with IAV, H5F-OMV immunised mice were on day 28 anaesthetised and inoculated intra-nasally with 10$^3$ PFU influenza virus strain A/PR/8/34 (PR8, H1N1) in 50 µl sterile PBS. Weights were recoded of each animal from the day of challenge up until the end point at 33 days. At autopsy blood/serum and bronchoalveolar lavage fluid were taken for antibody and cytokine analyses and lung tissue was used to determine virus titre. For in vivo OMV trafficking studies, mice were intranasally administered Dio-labelled H5F-OMVs and 1 and 5 days later OMV acquisition and uptake by macrophage and dendritic cells in the BAL, nasal associated lymphoid tissue (NALT) and cervical and mediastinal lymph nodes was determined by flow cytometry.

Virus Quantitation

Plaque assay were performed on homogenates of lung tissue from PR8-infected mice largely as described previously [22]. Briefly, viral samples from lungs were titrated in a 10-fold serial dilution from 10$^1$ to 10$^6$ in DMEM supplemented with TPCK-trypsin. Each dilution was incubated with MDCK cells in individual wells of a 24 well plate for 1 hour at 37° C., 5% CO$_2$. The media was aspirated and replaced with overlay media containing 2.4% Avicel. Plates were incubated at 37° C., 5% CO2 for 72 hours. Avicel was aspirated and plates were washed and cells were fixed in acetone:methanol (60:40) for 10 min. Cells were allowed to air dry prior to staining with crystal violet for 10 minutes, washed and air dried. Plaques were counted then multiplied by dilution factor and volume of virus plated to give viral titre (PFU/ml).

Antibody ELISA

ELISA plates were coated with target antigens (UV inactivated PR8 virus, recombinant *Salmonella* OmpA or SseB) in 0.1M NaHCO$_3$ and incubated for 12-16 hours at 4° C. Plates were washed 3 times with PBS with 0.05% Tween 20 (PT), incubated with blocking solution (PBS with 2% BSA) for 3 h at 20° C., and washed 6 times with PT. BAL and serum samples and supernatants of homogenised faecal pellets (in phosphate-buffered saline (pH, 7.2) with soybean trypsin inhibitor (0.5 mg/mL; Sigma), phenylmethylsulfonyl fluoride (0.25 mg/mL; Sigma), 0.05 M EDTA, and 0.05% Tween 20 (Sigma)) diluted in PBS with 1% BSA, 0.05% Tween (PBT) were added to the plate wells and incubated for 12-16 h at 4° C. then washed 6 times with PT and incubated with PBT containing HRP-anti-mouse IgG (1:1000, Thermo-Fisher) or HRP-anti-mouse IgA (1:1000, Life Technologies) for 20 min at 20° C. Plates were washed 6 times with PT then incubated in the dark with TMB High Sensitivity substrate solution (BioLegend) for 30 min at 20° C. The reaction was stopped by the addition of 2 N H$_2$SO$_4$ and the optical density was measured at 450 nm using a TECAN infinite f50 spectrophotometer (Männedorf, Switzerland). Abcam's IgA Mouse ELISA Kit was used to determine total IgA in Salivary Glands and Bronchoalveolar lavages (BAL)

Flow Cytometry

Approximately 1×10$^6$ tissue-derived cells were incubated in PBS, 2% FCS (PBS-FCS) for 15 min at 4° C. prior to the addition of fluorochrome-conjugated monoclonal antibodies specific for CD11b (clone . . . , source), CD11c (clone . . . , source), MHC class II, (clone . . . , source) F4/80 (clone . . . , source), Singlec (clone . . . , source) or CD103 (clone . . . , source) in PBS-FCS and incubation for 30 min at 4° C. in the dark. Cells were then washed in PBS-FCS, fixed in PBS, 4% paraformaldehyde for 15 min at 20° C. prior to analysis on a MACSQuant Analyzer 10 (Miltenyi Biotech UK). Data were analysed using Weasel software (http://www.frankbattye.com.au).

Statistical Analysis

Data were subjected to D'Agostino & Pearson omnibus normality test. One-way ANOVA followed by a Dunnett's multiple comparison post hoc test was performed using GraphPad Prism 5 software (USA). Statistically significant differences between two mean values were established by a p-value<0.05. Data are presented as the mean±standard deviation (n=10).

Results

Characteristics and Physical Properties of Bt OMVs

Bt is a prominent Gram-negative anaerobe that is universal in nature, occupying multiple and varied habitats including the lower GI-tract of all vertebrates [23]. In humans it is the most prevalent and abundant bacterial species of the intestinal microbiota [24]. During its growth cycle OMVs bud off from the outer membrane (FIG. 1*a*) and are recovered by a series of filtration and ultracentrifugations of early stationary growth phase cultures (see Material and Methods). Bt OMVs range in size from approximately 100 nm to greater than 400 nm with a mean size of 237 nm (FIG. 1*b*) and retain the characteristic double membrane of their parental cells (FIG. 1*c*). Bt OMVs are highly stable with minimal loss (<10% of total protein or heterologous protein) of luminal proteins detected after exposing OMVs to elevated ambient temperature (40° C.), acid, detergent, proteases, sonication and high pressure (FIG. 1*d* and data not shown).

Heterologous Bacterial, Viral and Human Proteins Expressed in Bt and Incorporated into OMVs To test whether the delivery of heterologous antigens into Bt OMVs is broadly applicable we selected candidate vaccine antigens for the important mucosal pathogens (*Salmonella typhimurium enterica* and influenza A virus; IAV) and therapeutic proteins (keratinocyte growth factor-2; KGF-2). For *S. typhi,* the outer membrane protein, OmpA, and the SPI-2 translocon subunit, SseB, were chosen as they elicit antibody and T cell responses and confer some degree of protective immunity in mice with antibody responses in humans being correlates of immune protection [25, 26, 27, 28, 29, 30, 31, 32, 33] For IAV, the H-stalk protein H5F of an H5N1 (VN/04:A/VietNam/1203/04) strain was selected as it confers robust protection against challenge with multiple IAV strains and can reduce lung viral titres by 3-fold [34, 35, 36]. KGF-2 is essential for epithelial cell proliferation and preserving the integrity of the intestinal mucosa [36], and has therapeutic potential for the treatment of inflammatory bowel disease [37].

Mini-genes encoding the bacterial, viral and human proteins were cloned downstream of sequences encoding N-terminal signal peptides from Bt genes whose products are contained within the lumen or outer membrane of OMVs (FIG. 2*a*) were constructed in *L. lactis* (for KGF-2) or *E. coli* (for OmpA, SseB and HF5) hosts and then mobilised into Bt via a triple filter mating protocol using a help strain. Immunoblotting of whole cell and OMV lysates of recombinant Bt strains confirmed expression of all three heterologous proteins with . . . (FIG. 2*c*). The luminal versus outer membrane distribution of the proteins in Bt OMVs was established using a protease protection assay which showed that *Salmonella* OmpA distribution was to the outer membrane whereas *Salmonella* SseB, influenza HF5 and KGF-2 were contained within the lumen of OMVs. Whereas OmpA and H5F were readily detectable in OMV lysates by immunoblotting, SseB was undetectable by this method and instead we relied on proteomics to confirm its' expression in the lumen of OMVs (data not shown).

Bt OMVs have Inherent Adjuvanticity

Many conventional vaccines rely on the inclusion of adjuvants to enhance their immunogenicity and to reduce the number of doses and amount of antigen (or pathogen component) required to elicit a protective immune response, particularly in immunocompromised people [2, 38]. To formally evaluate the adjuvant properties of Bt OMVs, mice were administered a single dose of native OMVs via the intranasal route and 5 days later lymphoid tissues of the upper and lower respiratory tract (NALT and BALT, respectively) were harvested and analysed by immunohistology for the presence of organised lymphoid structures and follicles indicative of an active immune response. The images in FIG. 3 show the presence of large organised lymphoid follicles in both the NALT (3*b* and *d*) and BALT (3*c*) that contain dendritic cells, T cells and large numbers of B cells. Of note, OMVs were also effective at eliciting the formation of fat associated lymphoid clusters (FALC) in the lung parenchyma (3*e*). Consistent with the immune response priming ability of Bt OMVs, within 24 h of intranasally administering (fluorescent labelled) OMVs it was possible to detect them in macrophages and dendritic cells in both the lung and draining cervical and mediastinal lymph nodes (FIG. 15), which are major inductive sites of cell- and humoral-mediated immune responses.

From a biosafety perspective, neither orally nor intranasally administered native OMVs or vaccine antigen formulated OMVs had no adverse health effects with no tissue pathology evident in treated animals at post mortem (data not shown). Orally administered OMVs also had no or a small and/or transient effect on intestinal microbes as determined from culturing faecal samples on selective media (FIG. 16).

Based upon these findings and clear evidence of the inherent adjuvanticity of Bt OMVs, we predicted that mucosally administered OMV vaccine formulations will be effective at eliciting both (vaccine) antigen specific antibodies in mucosal sites and systemically.

Mucosal Delivery of OMV Vaccine Formulations

We initially used OMV *Salmonella* vaccine antigen (St-OmpA and St-SseB) preparations to compare and contrast different formulations and routes of administration. St-OmpA and St-SseB expressing OMVs were administered to mice via the oral or nasal routes using the dosing regimen depicted in FIG. 4*a*. For reference, OMV formulations were also administered parenterally. At the end of the experiment serum and BAL samples were analysed for antigen-specific IgA (mucosal) and IgG (serum) antibodies by ELISA. For serum antibody responses, the data displayed in FIG. 4*b* shows that for St-OmpA OMVs the intraperitoneal route of administration generated the highest levels of antigen specific IgG antibodies in the serum compared to the oral or intranasal routes of delivery, for which comparable and low levels of St-OmpA specific IgG were detected. For St-SseB OMVs, the intranasal route of administration generated significantly higher levels of antigen specific serum IgG antibodies compared to orally delivered OMVs ($p<0.001$) that were equivalent to the levels of antigen-specific IgG seen after intraperitoneal immunisation. For mucosal IgA antibody responses, intranasally administered St-OmpA and St-SseB OMVs were equally effective at eliciting antigen specific IgA antibodies in the lower respiratory tract and BAL (FIG. 4*c*). Of note, there was more individual variation in the IgA levels and response to St-OmpA OMVs compared to animals administered St-SseB OMVs. Despite the induction of *Salmonella* antigen specific IgG antibodies, neither oral nor parenteral vaccination with StOmpA-OMVs conferred significant levels of protection to *Salmonella* infection as judged by the pathogen burden (CFU) in intestinal and extra-intestinal tissues at the end of the study and 5 days post infection (FIG. 17). We concluded therefore that StOmpA-OMV formulated vaccines delivered orally (or parenterally) are unable to protect against oral *Salmonella* infection.

Based on the potent adjuvant effect of intranasally administered OMVs (FIG. 3) and higher levels of antigen specific mucosal and systemic antigen specific antibodies after intranasal immunisation with OMV based vaccines (FIGS. 4*b* and *c*), we investigated further the possibility that intranasal immunisation with OMV-based vaccines is, compared to oral immunisation, a better option for conferring protection to infectious challenge.

Intranasal OMV Viral Vaccine Formulations Protect Against Pulmonary IAV Infection HF5 containing OMVs (approximately 0.5 ug/dose) were administered intranasally to mice followed by two further doses on days 7 and 14. Control mice received either native OMVs or vehicle (PBS) alone. On day 28 all groups of mice were given intranasally $10^3$ PFU of A/PR/8/34 (PR8) H1N1 strain of IAV, which is unrelated to the H5N1 strain of origin of H5F vaccine antigen. At the end point on day 33, serum and BAL were collected for assessing anti-viral antibody responses and the lungs were processed for virus titre. During infection the body weight of all groups of infected animals declined with the greatest weight loss seen in control, PBS administered, animals that exhibited a 20% decrease in weight (FIG. 5*a*). Animals immunised with native OMVs displayed a more gradual decline in weight after infection, similar to that in H5F-OMV immunised animals. Notably, the body weight of the H5F-OMV immunised animals increased between day 4 and 5 post-infection indicative of a less severe, and recovery from, infection. This was confirmed from the lung viral titre data (FIG. 5*b*). The viral load of animals immunised with H5F-OMVs was significantly lower ($p<0.006$) than that of the other groups, reflecting an approximate 7 to 8-fold lower level of virus. Consistent with lower viral load in the lungs of H5F-OMV immunised animals, BAL H5F specific IgG antibody levels were significantly higher ($p=0.004$) in this group of animals compared to the other groups (FIG. 5*c*). Serum anti-H5F IgG antibody levels were also higher in H5F-OMV immunised animals compared to the other groups although the differences did not reach statistical significance ($p=0.057$).

KGF-2 Containing OMVs Protect Against Acute Colitis

To determine the suitability of Bt OMVs for mucosal delivery of therapeutic proteins, the human KGF-2 protein was expressed in Bt OMVs by cloning a mini gene containing the coding sequence of the mature human kgf-2 gene and the Bt OmpA signal peptide in Bt (Bt-KGF). Immunoblotting of lysates of OMVs harvested from cultures of Bt-KGF (KGF-OMV) established that they contained approximately 5 ug/ml of KGF-2 and that the protein was contained within the lumen of OMVs (FIG. 2*b*). The biological activity of KGF-OMVs was confirmed in an epithelial cell wounding (scratch) assay in which the addition of intact KGF-OMVs to the epithelial cell cultures promoted epithelial cell proliferation and accelerated wound closure (FIG. 18). KGF-OMVs were tested in the acute murine DSS colitis model, which is a well characterised, simple and reproducible model of intestinal inflammation that is independent of lymphocyte-mediated responses and in which the clinical severity can be quantified and new therapeutic agents evaluated [39]. Since DSS primarily affects epithelial cells and inhibits their proliferation [39] this model is well suited to testing the therapeutic potential of KGF-OMVs. The design of this study is shown in FIG. 6*a:* DSS (2.5% w/v) was added to the drinking water for 7 days after which mice were given normal drinking water. On days 1, 3 and 5 mice were orally administered native OMVs or KGF-OMVs (containing approximately 0.5 ug KGF/dose), or vehicle (PBS) alone. The dosing regimen was based in part on our previous studies using a *B. ovatus* strain engineered to express human KGF-2 in vivo that had a therapeutic effect in DSS-colitis [40], and on pilot experiments to assess the tolerability of OMVs (data not shown).

KGF-OMVs controlled colitis both clinically and pathologically. Weight loss was significantly reduced in animals receiving KGF-OMVs compared to non-treated animals ($p<0.01$) or animals administered native OMVs ($p<0.001$) (FIG. 6*b*). KGF-OMVs also reduced the impact of DSS on colon shrinkage and reduction in length (FIGS. 6*c* and *e*), which is an independent measure of inflammation [41]. Consistent with the therapeutic effect of KGF-OMVs, disease activity index scores were significantly lower in KGF-OMV-treated animals compared to other treatment groups (FIG. 6*d* and Supplementary Tables 1 and 2). Histopathology showed that KGF-OMV treatment reduced epithelial damage and inflammatory infiltrate compared to non-treated mice and mice administered native OMVs (FIG. 7a). KGF-OMVs also had a beneficial effect on mucin-producing goblet cells. Compared to non-treated animals or animals receiving native OMVs there was a significant increase in the number of mucin-containing goblet cells in the colonic mucosa of KGF-OMV treated animals (FIG. 7b) with the appearance and distribution of goblet cells resembling that of control animals receiving water alone and no DSS (FIG. 7c).

Discussion

In this study we have provided evidence for the suitability of using OMVs from the major human gut commensal bacteria, Bt, to deliver biologics to mucosal sites to protect against infection and injury. The nanosize and non-replicative status of Bt OMVs together with their stability and ability to interact with mucosal and systemic host cells makes them ideally suited for drug delivery. Moreover, they possess innate adjuvant properties and the ability to activate immune cells of both the innate and adaptive immune system. The use of OMVs from prominent human commensal bacteria that have established a mutualistic relationship with, and are well tolerated by, their host is also desirable from a safety perspective and in minimising or preventing inappropriate host responses; as evidenced by the absence of any change in health status or pathology in Bt-OMV treated animals.

The Bt OMV technology platform is underpinned by our ability to engineer *Bacteroides* sp. [21, 42, 43] to express heterologous proteins that retain their biological activity [40, 44, 45], and through the use of specific protein secretion sequences to direct them to the periplasmic space for export and incorporating into the lumen or outer membrane of Bt generated OMVs. Whilst it has not been possible to define the minimum or optimal level of expression of heterologous proteins in Bt OMVs required to elicit an appropriate host response, low levels of expression only detectable by high resolution LC-MS based proteomics, as for *Salmonella* SseB, are sufficient to induce robust host mucosal and systemic antibody responses. There was therefore no apparent correlation between the levels of expression of different proteins within or at the surface of OMVs and their ability to elicit a host response. Determining the amount of biologically active protein in OMV formulations was also made difficult by their resilience and ability to resist disruption by high pressure, acid, detergent, proteases or sonication. OMV cargo does however become accessible after uptake by host cells [8], most likely as a result of an OMV-intracellular membrane fusion event [12].

The majority of OMV applications have to date focused on vaccine development [18] as they offer significant advantages over conventional vaccines; they are non-replicating, provide needle-free delivery, target mucosal sites, have an established safety record, can elicit innate and antigen-specific adaptive immune responses, possess self-adjuvant properties (i.e. MAMPs such as LPS), and are relatively cheap and straightforward to produce. The limitations of current (non-comensal and pathogen-derived) OMV vaccines are the potential for unintended toxicity due to associated toxins, low expression levels of protective antigens, variable efficacy depending on source and formulation, the need for exogenous adjuvants, and provide only incomplete protection because of strain variation. Our work here demonstrates that these limitations can to a large extent be overcome through the use of bioengineered Bt OMVs. The intranasal route of administration was superior to oral administration in terms of eliciting high levels of *Salmonella* vaccine antigen-specific mucosal IgA and systemic IgG. This difference most likely reflects anatomical differences and the ease and effectiveness of accessing host immune inductive sites and their acquisition by mucosa-associated antigen presenting cells in the lower gastrointestinal tract versus the respiratory tract. With smaller distances to travel in the less harsh environment of the lungs, OMVs can more readily access host cells; within 24 h of intranasal administration Bt OMVs were acquired by macrophages (CD11b$^+$, F/480$^+$) and dendritic cells (CD11c$^+$) in the mocusa of the upper and lower respiratory tract, with some trafficking to draining lymph nodes.

The failure to demonstrate protection to infectious challenge in animals immunised with *Salmonella* OMV vaccine formulations could be a consequence of various factors including sub-optimal expression of appropriate amounts of immunogenic OmpA antigen in Bt OMVs and the generation of sufficient (therapeutic) levels of functional, pathogen-neutralising, antibodies. Although St OmpA was previously identified as a potential cross-species vaccine candidate [46] our findings are in line with those of Okamura and colleagues [47] who found no protection in chickens parenterally immunised with StOmpA. However, the universal adjuvant properties of Bt OMVs suggests they may still be of value in *Salmonella* vaccine formulations as an adjuvant analogous to meningococcal OMVs that provide potent adjuvanticity to *N. meningitidis* protein vaccines [48, 49].

More compelling evidence for the use of Bt OMV based vaccines was obtained using OMV-H5F vaccines, which after intranasal administration conferred a significant level of heterotypic protection against an unrelated strain of IAV. Native OMVs appeared to reduce lung viral titres compared to non-treated/vaccinated animals which may be related to their potent adjuvant properties and the activation of innate and adaptive immune responses, including raised total IgA antibody levels in the upper and lower respiratory tract that would aid in strengthening front line protection against IAV infection [50]. At 5 days post challenge the average weight of the H5F-OMV immunized animals group increased, indicating possible recovery from virus infection, consistent with a 7-8-fold lower lung viral titre compared to other treatment groups. Future refinements to the study protocol should provide a clearer picture of the efficacy of OMV-H5F vaccines in preventing IAV infection by both homotypic and heterotypic strains of influenza virus. As our study was not an end point study we cannot directly compare the level of protection conferred by OMV-H5F vaccines against infectious challenge with similar studies trialing OMV-based vaccines; such as those of Watkins and colleagues [51] that developed *E. coli* OMV-IAV vaccines and obtained 100% protection in a murine lethal infectious challenge model. Collectively, our data provides the rationale and justification for the continuing development and refinement of the OMV technology to improve and optimise their vaccine capabilities and performance.

Our findings using KGF-containing OMVs to ameliorate experimental colitis demonstrates the potential for a broader portfolio of applications and in particular, for the mucosal delivery of therapeutic proteins for the treatment of non-infectious, autoimmune-driven pathologies. Bt OMVs expressing human KGF-2 were effective at ameliorating epithelial injury in a chemical (DSS) induced mouse model of acute colitis, at doses (0.5 ug/dose). The benefit of this form of drug delivery is exemplified by comparing the dose required to improve colonic pathology. The dose of KGF-OMVs (0.5-1.5 ug) used to achieve a significant reduction in colonic histopathology (FIG. 7a) is 1-2 orders of magnitude lower than that required via daily injection (20-100 ug for 7 days) to achieve a comparable reduction in colonic pathology [52, 53]. Also, the ability to deliver the protein directly to the target tissue using orally administered OMVs reduces the risk of side effects associated with systemic delivery.

In summary, our data adds to the different approaches being developed to express heterologous proteins in bacterial microvesicles [18] for a variety of applications and provides evidence for the utility and effectiveness of using human commensal bacteria as a source of bioengineered OMVs for the mucosal delivery of different biologics.

TABLE 102

Bacteria strains

| Species | Strain | Plasmid | Protein expressed | Antibiotic selection* | Reference |
|---|---|---|---|---|---|
| E. coli | Rosetta 2(DE3) pLysS | pGH165 | St OmpA | Amp, Cm | This study |
|  | Rosetta 2(DE3) pLysS | pGH201 | St SseB | Amp, Cm | This study |
| Bt | VPI-5482 |  |  |  | DMSZ Collection |
|  | GH290 |  |  | Tet | This study |
|  | GH490 | pGH090 |  | Ery | [54] |
|  | GH484 | pGH182 | St OmpA | Ery | This study |
|  | GH486 | pGH183 | St SseB | Ery | This study |
|  | GH474 | pGH173 | Hu. KGF-2 | Ery | This study |
|  | GH503 | pGH184 | IAV H5F | Ery | This study |
| S. typhimurim | SL1344 |  |  |  |  |

*Amp = ampicillin; Cm = chloramphenicol; Tet = tetracycline; Ery = erythromycin

TABLE 102

Primer sequences

| Primer | Sequence (5'→3')$^a$ |
|---|---|
| f-5'ompA_SphI | ATCTGCATGCTTTCGAGGAAGAACCGATGGTTGC |
| r-5'ompA_SalI | ATACGTCGACAATATAGCGGACTGCAATCC |
| f-3'ompA_BamHI | ACTTGGATCCTTCTGAATCGTGTGGTATTGG |
| r-3'ompA_SacI | ACTAGAGCTCATCTGTAGAGAAGAAACGGG |
| SPBTOmpA_fwd | CATGTTGCTGGCTTTTGCCGGCGTTGCGTCTGTC GCTTCTGCGCAGCAAACCGTGACTGTAACTGAAT ACGAGGTTATTCATATGTGACG |
| SPBTOmpA_rev | AATTCGTCACATATGAATAACCTCGTATTCAGTT ACAGTCACGGTTTGCTGCGCAGAAGCGACAGACG CAACGCCGGCAAAAGCCAGCAA |
| OmpAST_fwd | TGACCATATGGCTCCGAAAGATAACACC |
| OmpAST_rev | GTCAGAATTCTTAAGCCTGCGGCTGAGTTA |
| SseB_fwd | TGACCATATGTCTTCAGGAAACATCTT |
| SseB_rev | TGACGAATTCATGAGTACGTTTTCTGCG |
| XhoI_STOmpA_rev | ATATCTCGAGGAAACTTAAGCCTGCGG |
| XhoI_SseB_rev | ATATCTCGAGATGAGTACGTTTTCTGCG |

TABLE S1

Disease Activity Index (DAI) criteria and scoring

| Weight loss | Stool consistency | Bleeding | Caecum & colon appearance | Caecum & colon contents appearance | Score |
|---|---|---|---|---|---|
| <1% | Well-formed pellets | None | Normal | Regular shape | 0 |

TABLE S1-continued

Disease Activity Index (DAI) criteria and scoring

| Weight loss | Stool consistency | Bleeding | Caecum & colon appearance | Caecum & colon contents appearance | Score |
|---|---|---|---|---|---|
| 1-5% |  |  | White, abnormal size, strictures | Irregular but formed | 1 |
| 5-10% | Loose | Slight |  | Random shape | 2 |
| 10-15% |  |  |  | Blood in colon | 3 |
| >15% | Diarrhoea | Gross |  | Blood in caecum | 4 |

TABLE S2

Colon histology scoring

| Category | Criteria |  | Score |
|---|---|---|---|
| Inflammatory cell infiltrate | Severity | No infiltration | 0 |
|  |  | Minimal 0-10% | 1 |
|  |  | Mild 10-25% | 2 |
|  |  | Moderate 26-50% | 3 |
|  |  | Marked >51% | 4 |
|  | Extent | No infiltration | 0 |
|  |  | Mucosal | 1 |
|  |  | Mucosal and submucosal | 2 |
|  |  | Mucosal, submucosal and transmural | 3 |
| Presence of oedema | Extent | No oedema | 0 |
|  |  | in 0 to 25% of the section | 1 |
|  |  | in 26 to 50% of the section | 2 |
|  |  | in more than 51% of the section | 3 |
| Epithelial changes | Goblet cell loss | None or increase | 0 |
|  |  | Minimal: 0-20% | 2 |
|  |  | Mild: 21-35% | 3 |
|  |  | Moderate: 36-50% | 4 |
|  |  | Marked: >50% | 5 |
|  | Erosion | Absence | 0 |
|  |  | Presence | 1 |
| Mucosal architecture | Extent | Irregular crypts | 4 |
|  |  | Crypt loss | 5 |

REFERENCES 1

1. Williamson E D, Flick-Smith H C, Waters E, Miller J, Hodgson I, Le Butt C S, et al. Immunogenicity of the rF1+rV vaccine for plague with identification of potential immune correlates. Microb Pathogenesis. 2007; 42(1):11-21. doi: 10.1016/j.micpath.2006.09.003. PubMed PMID: WOS:000243431200002.
2. Smiley S T. Cell-mediated defense against *Yersinia pestis* infection. Adv Exp Med Biol. 2007; 603:376-86. Epub 2007/10/31. doi: 10.1007/978-0-387-72124-8_35. PubMed PMID: 17966434.
3. Williamson E D. Plague. Vaccine. 2009; 27 Suppl 4:D56-60. Epub 2009/10/20. doi: 10.1016/j.vaccine.2009.07.068. PubMed PMID: 19837288.
4. Meyer K F, Cavanaugh D C, Bartelloni P J, Marshall J D, Jr. Plague immunization. I. Past and present trends. J Infect Dis. 1974; 129:Suppl:S13-8. PubMed PMID: 4596516.
5. Parkhill J, Wren B W, Thomson N R, Titball R W, Holden M T, Prentice M B, et al. Genome sequence of *Yersinia pestis*, the causative agent of plague. Nature. 2001; 413 (6855):523-7. Epub 2001/10/05. doi: 10.1038/35097083. PubMed PMID: 11586360.
6. Quenee L E, Schneewind O. Plague vaccines and the molecular basis of immunity against *Yersinia pestis*. Hum Vaccin. 2009; 5(12):817-23. Epub 2009/09/30. PubMed PMID: 19786842.
7. Williamson E D, Flick-Smith H C, Lebutt C, Rowland C A, Jones S M, Waters E L, et al. Human immune response to a plague vaccine comprising recombinant F1 and V antigens. Infection and immunity. 2005; 73(6):3598-608. Epub 2005/05/24. doi: 10.1128/IAI.73.6.3598-3608.2005. PubMed PMID: 15908389; PubMed Central PMCID: PMCPMC1111881.
8. Oyston P C, Williamson E D. Prophylaxis and therapy of plague. Expert Rev Anti Infect Ther. 2013; 11(8):817-29. Epub 2013/08/28. doi: 10.1586/14787210.2013.814432. PubMed PMID: 23977937.
9. Feodorova V A, Corbel M J. Prospects for new plague vaccines. Expert Rev Vaccines. 2009; 8(12):1721-38. Epub 2009/12/01. doi: 10.1586/erv.09.129. PubMed PMID: 19943765.
10. Saroja C, Lakshmi P, Bhaskaran S. Recent trends in vaccine delivery systems: A review. Int J Pharm Investig. 2011; 1(2):64-74. Epub 2011/04/01. doi: 10.4103/2230-973X.82384. PubMed PMID: 23071924; PubMed Central PMCID: PMCPMC3465129.
11. Zhao L, Seth A, Wibowo N, Zhao C X, Mitter N, Yu C, et al. Nanoparticle vaccines. Vaccine. 2014; 32(3):327-37. Epub 2013/12/04. doi: 10.1016/j.vaccine.2013.11.069. PubMed PMID: 24295808.
12. Singh M, Chakrapani A, O'Hagan D. Nanoparticles and microparticles as vaccine-delivery systems. Expert Rev Vaccines. 2007; 6(5):797-808. Epub 2007/10/13. doi: 10.1586/14760584.6.5.797. PubMed PMID: 17931159.
13. Gerritzen M J H, Martens D E, Wijffels R H, van der Pol L, Stork M. Bioengineering bacterial outer membrane vesicles as vaccine platform. Biotechnol Adv. 2017; 35(5):565-74. Epub 2017/05/20. doi: 10.1016/j.biotechadv.2017.05.003. PubMed PMID: 28522212.
14. McBroom A J, Kuehn M J. Release of outer membrane vesicles by gram-negative bacteria is a novel envelope stress response. Molecular Microbiology. 2007; 63(2):545-58. doi: 10.1111/j.1365-2958.2006.05522.x. PubMed PMID: WOS:000243305300019.
15. Jeannin P, Magistrelli G, Goetsch L, Haeuw J F, Thieblemont N, Bonnefoy J Y, et al. Outer membrane protein A (OmpA): a new pathogen-associated molecular pattern that interacts with antigen presenting cells-impact on vaccine strategies. Vaccine. 2002; 20:A23-A7. doi: Pii S0264-410x(02)00383-3 Doi 10.1016/S0264-410x(02)00383-3. PubMed PMID: WOS:000180160200004.
16. Alaniz R C, Deatherage B L, Lara J C, Cookson B T. Membrane vesicles are immunogenic facsimiles of *Salmonella typhimurium* that potently activate dendritic cells, prime B and T cell responses, and stimulate protective immunity in vivo. Journal of Immunology. 2007; 179(11):7692-701. PubMed PMID: WOS: 000251378300058.
17. Stephens D S, Edwards K M, Morris F, Mcgee Z A. Pili and Outer-Membrane Appendages on *Neisseria meningitidis* in the cerebrospinal fluid of an infant. Journal of Infectious Diseases. 1982; 146(4):568-. PubMed PMID: WOS:A1982PM54500022.
18. Collins B S. Gram-negative Outer membrane vesicles in vaccine development. Discovery Medicine. 2011; 62:7-15. PubMed PMID: WOS:000208639700001.
19. de Kleijn E D, de Groot R, Labadie J, Lafeber A B, van den Dobbelsteen G, van Alphen L, et al. Immunogenicity and safety of a hexavalent meningococcal outer-membrane-vesicle vaccine in children of 2-3 and 7-8 years of age. Vaccine. 2000; 18(15):1456-66. doi: Doi 10.1016/S0264-410x(99)00423-5. PubMed PMID: WOS: 000085195800005.
20. Sandbu S, Feiring B, Oster P, Helland O S, Bakke H S W, Naess L M, et al. Immunogenicity and safety of a combination of two serogroup B meningococcal outer membrane vesicle vaccines. Clinical and Vaccine Immunology. 2007; 14(9):1062-9. doi: 10.1128/CVI.00094-07. PubMed PMID: WOS:000249488400002.
21. Kaparakis-Liaskos M, Ferrero R L. Immune modulation by bacterial outer membrane vesicles. Nat Rev Immunol. 2015; 15(6):375-87. doi: 10.1038/nri3837. PubMed PMID: 25976515.
22. Hickey C A, Kuhn K A, Donermeyer D L, Porter N T, Jin C, Cameron E A, et al. Colitogenic *Bacteroides thetaiotaomicron* antigens access host immune cells in a sulfatase-dependent manner via outer membrane vesicles. Cell Host Microbe. 2015; 17(5):672-80. doi: 10.1016/j.chom.2015.04.002. PubMed PMID: 25974305; PubMed Central PMCID: PMC4432250.
23. Shoemaker N B, Getty C, Gardner J F, Salyers A A. Tn4351 Transposes in *Bacteroides* spp and mediates the integration of plasmid R751 into the *Bacteroides* chromosome. Journal of Bacteriology. 1986; 165(3):929-36. PubMed PMID: WOS:A1986A276700039.
24. Graham V A, Hatch G J, Bewley K R, Steeds K, Lansley A, Bate S R, et al. Efficacy of primate humoral passive transfer in a murine model of pneumonic plague is mouse strain-dependent. J Immunol Res. 2014; 2014:807564. doi: 10.1155/2014/807564. PubMed PMID: 25097863; PubMed Central PMCID: PMCPMC4109106.
25. Wegmann U, Horn N, Carding S R. Defining the *Bacteroides* ribosomal binding site. Applied and Environmental Microbiology. 2013; 79(6):1980-9. doi: 10.1128/Aem.03086-12. PubMed PMID: WOS: 000315454500026.
26. Williamson E D, Packer P J, Waters E L, Simpson A J, Dyer D, Hartings J, et al. Recombinant (F1+V) vaccine protects cynomolgus macaques against pneumonic plague. Vaccine. 2011; 29(29-30):4771-7. Epub 2011/05/17. doi: 10.1016/j.vaccine.2011.04.084. PubMed PMID: 21570437.
27. Hill J, Leary S E, Griffin K F, Williamson E D, Titball R W. Regions of *Yersinia pestis* V antigen that contribute to protection against plague identified by passive and active immunization. Infect Immun. 1997; 65(11):4476-82. Epub 1997/11/14. PubMed PMID: 9353022; PubMed Central PMCID: PMCPMC175643.
28. Sawa T, Katoh H, Yasumoto H. V-antigen homologs in pathogenic gram-negative bacteria. Microbiol Immunol. 2014; 58(5):267-85. Epub 2014/03/20. doi: 10.1111/1348-0421.12147. PubMed PMID: 24641673.
29. Frank D W, Vallis A, Wiener-Kronish J P, Roy-Burman A, Spack E G, Mullaney B P, et al. Generation and characterization of a protective monoclonal antibody to *Pseudomonas aeruginosa* PcrV. J Infect Dis. 2002; 186(1):64-73. Epub 2002/06/29. doi: 10.1086/341069. PubMed PMID: 12089663.
30. Goure J, Broz P, Attree O, Cornelis G R, Attree I. Protective anti-V antibodies inhibit *Pseudomonas* and *Yersinia* translocon assembly within host membranes. J Infect Dis. 2005; 192(2):218-25. Epub 2005/06/18. doi: 10.1086/430932. PubMed PMID: 15962216.
31. Sawa T, Ito E, Nguyen V H, Haight M. Anti-PcrV antibody strategies against virulent *Pseudomonas aeruginosa*. Hum Vaccin Immunother. 2014; 10(10):2843-52. Epub 2014/12/09. doi: 10.4161/21645515.2014.971641. PubMed PMID: 25483637; PubMed Central PMCID: PMCPMC5443083.
32. Africa W. Plague Outbreak Madagascar. WHO, 2017.
33. Pouliot K, Pan N, Wang S, Lu S, Lien E, Goguen J D. Evaluation of the role of LcrV-Toll-like receptor 2-mediated immunomodulation in the virulence of *Yersinia pestis*. Infect Immun. 2007; 75(7):3571-80. Epub 2007/04/18. doi: 10.1128/IAI.01644-06. PubMed PMID: 17438030; PubMed Central PMCID: PMCPMC1932965.
34. Heath D G, Anderson G W, Jr., Mauro J M, Welkos S L, Andrews G P, Adamovicz J, et al. Protection against experimental bubonic and pneumonic plague by a recombinant capsular F1-V antigen fusion protein vaccine. Vaccine. 1998; 16(11-12):1131-7. Epub 1998/07/31. PubMed PMID: 9682370.
35. Moore B D, New R R C, Butcher W, Mahood R, Steward J, Bayliss M, et al. Dual route vaccination for plague with emergency use applications. Vaccine. 2018. Epub 2018/07/19. doi: 10.1016/j.vaccine.2018.06.039. PubMed PMID: 30017148.
36. Bai X, Findlow J, Borrow R. Recombinant protein meningococcal serogroup B vaccine combined with outer membrane vesicles. Expert Opin Biol Ther. 2011; 11(7):969-85. Epub 2011/05/28. doi: 10.1517/14712598.2011.585965. PubMed PMID: 21615224.
37. Zav'yalov V P, Chernovskaya T V, Navolotskaya E V, Karlyshev A V, MacIntyre S, Vasiliev A M, et al. Specific high affinity binding of human interleukin 1 beta by Caf1A usher protein of *Yersinia pestis*. FEBS Lett. 1995; 371(1):65-8. Epub 1995/08/28. PubMed PMID: 7664886.
38. Elvin S J, Williamson E D. Stat 4 but not Stat 6 mediated immune mechanisms are essential in protection against plague. Microb Pathog. 2004; 37(4):177-84. Epub 2004/10/02. doi: 10.1016/j.micpath.2004.06.009. PubMed PMID: 15458778.
39. Christodoulides M, Heckels J. Novel approaches to *Neisseria meningitidis* vaccine design. Pathog Dis. 2017; 75(3). Epub 2017/04/04. doi: 10.1093/femspd/ftx033. PubMed PMID: 28369428.
40. Alves N J, Turner K B, Medintz I L, Walper S A. Protecting enzymatic function through directed packaging into bacterial outer membrane vesicles. Sci Rep. 2016; 6:24866. Epub 2016/04/28. doi: 10.1038/srep24866. PubMed PMID: 27117743; PubMed Central PMCID: PMCPMC4846811.

REFERENCES 2

1. Kulp A, Kuehn M J. Biological Functions and Biogenesis of Secreted Bacterial Outer Membrane Vesicles. Annual Review of Microbiology, Vol 64, 2010. 2010; 64:163-184. doi: Doi 10.1146/Annurev.Micro.091208.073413. PubMed PMID: WOS:000284030600009; English.
2. Del Giudice G, Rappuoli R, Didierlaurent A M. Correlates of adjuvanticity: A review on adjuvants in licensed vaccines. Semin Immunol. 2018 May 22. doi: 10.1016/j.smim.2018.05.001. PubMed PMID: 29801750.
3. Ellis T N, Kuehn M J. Virulence and Immunomodulatory Roles of Bacterial Outer Membrane Vesicles. Microbiology and Molecular Biology Reviews. 2010 March; 74(1):81-+. doi: Doi 10.1128/Mmbr.00031-09. PubMed PMID: WOS:000275120100004; English.
4. Haurat M, Elhenawy W, Feldman M. Prokaryotic membrane vesicles: new insights on biogenesis and biological roles. Biol Chem. 2014; 396(2):95-109.
5. Olsen I, Amano A. Outer membrane vesicles—offensive weapons or good Samaritans? J Oral Microbiol. 2015; 7:27468. doi: 10.3402/jom.v7.27468. PubMed PMID: 25840612; PubMed Central PMCID: PMCPMC4385126.
6. Elhenawy W, Debelyy M O, Feldman M F. Preferential packing of acidic glycosidases and proteases into *Bacteroides* outer membrane vesicles. MBio. 2014; 5(2):e00909-14. doi: 10.1128/mBio.00909-14. PubMed PMID: 24618254; PubMed Central PMCID: PMC3952158.
7. Rakoff-Nahoum S, Coyne M J, Comstock L E. An ecological network of polysaccharide utilization among human intestinal symbionts. Curr Biol. 2014 Jan. 6; 24(1):40-9. doi: 10.1016/j.cub.2013.10.077. PubMed PMID: 24332541; PubMed Central PMCID: PMC3924574.
8. Stentz R, Osborne S, Horn N, et al. A bacterial homolog of a eukaryotic inositol phosphate signaling enzyme mediates cross-kingdom dialog in the mammalian gut. Cell Rep. 2014 Feb. 27; 6(4):646-56. doi: 10.1016/j.celrep.2014.01.021. PubMed PMID: 24529702; PubMed Central PMCID: PMC3969271.
9. Bryant W A, Stentz R, Le Gall G, et al. In Silico Analysis of the Small Molecule Content of Outer Membrane Vesicles Produced by *Bacteroides thetaiotaomicron* Indicates an Extensive Metabolic Link between Microbe and Host. Front Microbiol. 2017; 8:2440. doi: 10.3389/fmicb.2017.02440. PubMed PMID: 29276507; PubMed Central PMCID: PMCPMC5727896.
10. Shen Y, Giardino Torchia M L, Lawson G W, et al. Outer membrane vesicles of a human commensal mediate immune regulation and disease protection. Cell Host Microbe. 2012 Oct. 18; 12(4):509-20. doi: 10.1016/j.chom.2012.08.004. PubMed PMID: 22999859; PubMed Central PMCID: PMC3895402.
11. Hickey C A, Kuhn K A, Donermeyer D L, et al. Colitogenic *Bacteroides thetaiotaomicron* Antigens Access Host Immune Cells in a Sulfatase-Dependent Manner via Outer Membrane Vesicles. Cell Host Microbe. 2015 May 13; 17(5):672-80. doi: 10.1016/

12. Kaparakis-Liaskos M, Ferrero R L. Immune modulation by bacterial outer membrane vesicles. Nat Rev Immunol. 2015 June; 15(6):375-87. doi: 10.1038/nri3837. PubMed PMID: 25976515.
13. Stentz R, Carvalho A L, Jones E J, et al. Fantastic Voyage: The journey of intestinal microbiota-derived microvesicles through the body. Biochem Soc Trans. 2018; In Press.
14. Kesty N C, Kuehn M J. Incorporation of heterologous outer membrane and periplasmic proteins into *Escherichia coli* outer membrane vesicles. Journal of Biological Chemistry. 2004 Jan. 16; 279(3):2069-2076. doi: 10.1074/jbc.M307628200. PubMed PMID: WOS: 000188005700062; English.
15. Collins B S. Gram-negative Outer Membrane Vesicles in Vaccine Development. Discovery Medicine. 2011 July; 62:7-15. PubMed PMID: WOS:000208639700001; English.
16. de Kleijn E D, de Groot R, Labadie J, et al. Immunogenicity and safety of a hexavalent meningococcal outer-membrane-vesicle vaccine in children of 2-3 and 7-8 years of age. Vaccine. 2000 Feb. 14; 18(15):1456-1466. doi: Doi 10.1016/50264-410x(99)00423-5. PubMed PMID: WOS:000085195800005; English.
17. Sandbu S, Feiring B, Oster P, et al. Immunogenicity and safety of a combination of two serogroup B meningococcal outer membrane vesicle vaccines. Clinical and Vaccine Immunology. 2007 September; 14(9):1062-1069. doi: 10.1128/CVI.00094-07. PubMed PMID: WOS: 000249488400002; English.
18. Gerritzen M J H, Martens D E, Wijffels R H, et al. Bioengineering bacterial outer membrane vesicles as vaccine platform. Biotechnol Adv. 2017 September; 35(5): 565-574. doi: 10.1016/j.biotechadv.2017.05.003. PubMed PMID: 28522212.
19. Shoemaker N B, Getty C, Gardner J F, et al. Tn4351 Transposes in *Bacteroides* Spp and Mediates the Integration of Plasmid R751 into the *Bacteroides* Chromosome. Journal of Bacteriology. 1986 March; 165(3):929-936. PubMed PMID: WOS:A1986A276700039; English.
20. Stentz R, Horn N, Cross K, et al. Cephalosporinases associated with outer membrane vesicles released by *Bacteroides* spp. protect gut pathogens and commensals against beta-lactam antibiotics. J Antimicrob Chemother. 2015 March; 70(3):701-9. doi: 10.1093/jac/dku466. PubMed PMID: 25433011; PubMed Central PMCID: PMC4319488.
21. Wegmann U, Horn N, Carding S R. Defining the *Bacteroides* Ribosomal Binding Site. Applied and Environmental Microbiology. 2013 March; 79(6):1980-1989. doi: 10.1128/Aem.03086-12. PubMed PMID: WOS: 000315454500026; English.
22. Matrosovich M, Matrosovich T, Garten W, et al. New low-viscosity overlay medium for viral plaque assays. Virol J. 2006 Aug. 31; 3:63. doi: 10.1186/1743-422X-3-63. PubMed PMID: 16945126; PubMed Central PMCID: PMCPMC1564390.
23. Wexler H M. *Bacteroides:* the good, the bad, and the nitty-gritty. Clin Microbiol Rev. 2007 October; 20(4): 593-621. doi: 10.1128/CMR.00008-07. PubMed PMID: 17934076; PubMed Central PMCID: PMCPMC2176045.
24. Salyers A A. *Bacteroides* of the human lower intestinal tract. Annu Rev Microbiol. 1984; 38:293-313. doi: 10.1146/annurev.mi.38.100184.001453. PubMed PMID: 6388494.
25. Gil-Cruz C, Bobat S, Marshall J L, et al. The porin OmpD from nontyphoidal *Salmonella* is a key target for a protective B1b cell antibody response. Proceedings of the National Academy of Sciences of the United States of America. 2009 Jun. 16; 106(24):9803-9808. doi: 10.1073/pnas.0812431106. PubMed PMID: WOS: 000267045500047; English.
26. Kurtz J R, Petersen H E, Frederick D R, et al. Vaccination with a Single CD4 T Cell Peptide Epitope from a *Salmonella* Type III-Secreted Effector Protein Provides Protection against Lethal Infection. Infection and Immunity. 2014 June; 82(6):2424-2433. doi: 10.1128/IAI.00052-14. PubMed PMID: WOS:000336378100029; English.
27. Barat S, Willer Y, Rizos K, et al. Immunity to Intracellular *Salmonella* Depends on Surface-associated Antigens. Plos Pathogens. 2012 October; 8(10):e1002966. doi: ARTN e1002966 10.1371/journal.ppat.1002966. PubMed PMID: WOS:000310530300029; English.
28. Rollenhagen C, Sorensen M, Rizos K, et al. Antigen selection based on expression levels during infection facilitates vaccine development for an intracellular pathogen. Proceedings of the National Academy of Sciences of the United States of America. 2004 Jun. 8; 101(23):8739-8744. doi: 10.1073/pnas.0401283101. PubMed PMID: WOS:000222037000045; English.
29. McSorley S J, Cookson B T, Jenkins M K. Characterization of CD4(+) T cell responses during natural infection with *Salmonella typhimurium*. Journal of Immunology. 2000 Jan. 15; 164(2):986-993. PubMed PMID: WOS:000084708600057; English.
30. Paramasivam N, Linke D. ClubSub-P: cluster-based subcellular localization prediction for Gram-negative bacteria and archaea. Frontiers in Microbiology. 2011; 2:doi: 10.3389/fmicb.2011.00218. doi: Artn 218 10.3389/Fmicb.2011.00218. PubMed PMID: WOS: 000208863500226; English.
31. Burton N A, Schurmann N, Casse O, et al. Disparate Impact of Oxidative Host Defenses Determines the Fate of *Salmonella* during Systemic Infection in Mice. Cell Host & Microbe. 2014 Jan. 15; 15(1):72-83. doi: 10.1016/j.chom.2013.12.006. PubMed PMID: WOS: 000330854100010; English.
32. Lee S J, McLachlan J B, Kurtz J R, et al. Temporal Expression of Bacterial Proteins Instructs Host CD4 T Cell Expansion and Th17 Development. Plos Pathogens. 2012 January; 8(1):e1002499. doi: ARTN e1002499 10.1371/journal.ppat.1002499. PubMed PMID: WOS: 000300767100039; English.
33. Reynolds C J, Jones C, Blohmke C J, et al. The serodominant secreted effector protein of *Salmonella*, SseB, is a strong CD4 antigen containing an immunodominant epitope presented by diverse HLA class II alleles. Immunology. 2014 November; 143(3):438-446. doi: 10.1111/imm.12327. PubMed PMID: WOS: 000342894300013; English.
34. Mallajosyula V V, Citron M, Ferrara F, et al. Influenza hemagglutinin stem-fragment immunogen elicits broadly neutralizing antibodies and confers heterologous protection. Proc Natl Acad Sci USA. 2014 Jun. 24; 111(25): E2514-23. doi: 10.1073/pnas.1402766111. PubMed PMID: 24927560; PubMed Central PMCID: PMCPMC4078824.
35. Valkenburg S A, Mallajosyula V V, Li O T, et al. Stalking influenza by vaccination with pre-fusion headless HA mini-stem. Sci Rep. 2016 Mar. 7; 6:22666. doi: 10.1038/ srep22666. PubMed PMID: 26947245; PubMed Central PMCID: PMCPMC4780079.
36. Werner S. Keratinocyte growth factor: a unique player in epithelial repair processes. Cytokine Growth Factor Rev. 1998 June; 9(2):153-65. PubMed PMID: 9754709.
37. Baumgart D C, Sandborn W J. Inflammatory bowel disease: clinical aspects and established and evolving therapies. Lancet. 2007 May 12; 369(9573):1641-57. doi: 10.1016/S0140-6736(07)60751-X. PubMed PMID: 17499606.
38. Saroja C, Lakshmi P, Bhaskaran S. Recent trends in vaccine delivery systems: A review. Int J Pharm Investig. 2011 April; 1(2):64-74. doi: 10.4103/2230-973X.82384. PubMed PMID: 23071924; PubMed Central PMCID: PMCPMC3465129.
39. Dieleman L A, Ridwan B U, Tennyson G S, et al. Dextran sulfate sodium-induced colitis occurs in severe combined immunodeficient mice. Gastroenterology. 1994 December; 107(6):1643-52. PubMed PMID: 7958674.
40. Hamady Z Z, Scott N, Farrar M D, et al. Xylan-regulated delivery of human keratinocyte growth factor-2 to the inflamed colon by the human anaerobic commensal bacterium Bacteroides ovatus. Gut. 2010 April; 59(4):461-9. doi: 10.1136/gut.2008.176131. PubMed PMID: 19736360.
41. Okayasu I, Hatakeyama S, Yamada M, et al. A novel method in the induction of reliable experimental acute and chronic ulcerative colitis in mice. Gastroenterology. 1990; 98:694-702.
42. Hamady Z Z, Farrar M D, Whitehead T R, et al. Identification and use of the putative Bacteroides ovatus xylanase promoter for the inducible production of recombinant human proteins. Microbiology. 2008 October; 154 (Pt 10):3165-74. doi: 10.1099/mic.0.2008/019109-0. PubMed PMID: 18832322.
43. Wegmann U, Carvalho A L, Stocks M, et al. Use of genetically modified bacteria for drug delivery in humans: Revisiting the safety aspect. Sci Rep. 2017 May 23; 7(1):2294. doi: 10.1038/s41598-017-02591-6. PubMed PMID: 28536456; PubMed Central PMCID: PMCPMC5442108.
44. Farrar M, Whithead T R, Lan J, et al. Engineering of the gut commensal bacterium Bacteroides ovatus to produce and secrete biologically active murine interleukin-2 in response to xylan. J Appl Microbiol. 2005; 98:1191-1197.
45. Hamady Z Z, Scott N, Farrar M D, et al. Treatment of colitis with a commensal gut bacterium engineered to secrete human TGF-beta1 under the control of dietary xylan 1. Inflamm Bowel Dis. 2011 September; 17(9): 1925-35. doi: 10.1002/ibd.21565. PubMed PMID: 21830271.
46. Brandtzaeg P. Gate-keeper function of the intestinal epithelium. Benef Microbes. 2013 Mar. 1; 4(1):67-82. doi: 10.3920/BM2012.0024. PubMed PMID: 23257015.
47. Okamura M, Ueda M, Noda Y, et al. Immunization with outer membrane protein A from Salmonella enterica serovar Enteritidis induces humoral immune response but no protection against homologous challenge in chickens. Poult Sci. 2012 October; 91(10):2444-9. doi: 10.3382/ps.2012-02303. PubMed PMID: 22991526.
48. Sanders H, Feavers I M. Adjuvant properties of meningococcal outer membrane vesicles and the use of adjuvants in Neisseria meningitidis protein vaccines. Expert Rev Vaccines. 2011 March; 10(3):323-34. doi: 10.1586/erv.11.10. PubMed PMID: 21434800.
49. Moshiri A, Dashtbani-Roozbehani A, Najar Peerayeh S, et al. Outer membrane vesicle: a macromolecule with multifunctional activity. Hum Vaccin Immunother. 2012 July; 8(7):953-5. doi: 10.4161/hv.20166. PubMed PMID: 22699443.
50. Renegar K B, Small P A, Jr., Boykins L G, et al. Role of IgA versus IgG in the control of influenza viral infection in the murine respiratory tract. J Immunol. 2004 Aug. 1; 173(3):1978-86. PubMed PMID: 15265932.
51. Watkins H C, Rappazzo C G, Higgins J S, et al. Safe Recombinant Outer Membrane Vesicles that Display M2e Elicit Heterologous Influenza Protection. Mol Ther. 2017 Apr. 5; 25(4):989-1002. doi: 10.1016/j.ymthe.2017.01.010. PubMed PMID: 28215994; PubMed Central PMCID: PMCPMC5383554.
52. Zeeh J M, Procaccino F, Hoffmann P, et al. Keratinocyte growth factor ameliorates mucosal injury in an experimental model of colitis in rats. Gastroenterology. 1996 April; 110(4):1077-83. PubMed PMID: 8612996.
53. Miceli R, Hubert M, Santiago G, et al. Efficacy of keratinocyte growth factor-2 in dextran sulfate sodium-induced murine colitis. J Pharmacol Exp Ther. 1999 July; 290(1):464-71. PubMed PMID: 10381813.
54. Wegmann U, Horn N, Carding S R. Defining the Bacteroides ribosomal binding site. Applied and environmental microbiology. 2013 March; 79(6):1980-9. doi: 10.1128/aem.03086-12. PubMed PMID: 23335775; PubMed Central PMCID: PMCPMC3592243. eng.

The invention claimed is:

1. A mucosal vaccine delivered by oral and/or nasal administration for immunization against plague or Y. pestis infection in animals and humans wherein said vaccine comprises outer membrane vesicles (OMVs) including the V and/or F1 antigens of Y. pestis wherein the OMVs are produced by modified Bacteroides thetaiotaomicron (Bt) wherein the genes or mini-genes encoding the V and/or F1 Y. pestis antigens are cloned downstream of sequences encoding the N-terminal signal peptides of the Bt OMV protein OmpA.

2. A vaccine according to claim 1 wherein the genes or mini-genes encoding the V and/or F1 Y. pestis proteins are cloned downstream of sequences encoding the N-terminal signal peptides of the Bt OMV protein OmpA.

3. A vaccine according to claim 2 wherein the protein products are contained within the lumen or outer membrane of OMVs.

4. A vaccine according to claim 1 wherein the gene constructs are generated in E. coli hosts and then introduced into Bt.

5. A vaccine according to claim 1 wherein a synthetic gene construct encoding the V antigen and/or a synthetic operon construct encoding caf1M, caf1A and/or caf1 genes of the caf1 operon that generates the F1 protein are N-terminally fused to the OmpA signal peptide of Bt.

6. A vaccine according to claim 5 wherein gene cassettes are obtained through gene synthesis and subsequently cloned into the E. coli plasmid pEX-A2 and pEX-K4 respectively.

* * * * *